(12) United States Patent
Shoshihara et al.

(10) Patent No.: US 9,066,696 B2
(45) Date of Patent: Jun. 30, 2015

(54) SENSOR INSERTION/RECOVERY DEVICE

(75) Inventors: Tomohiro Shoshihara, Kyoto (JP); Yosuke Murase, Kyoto (JP); Akihiro Yamamoto, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 804 days.

(21) Appl. No.: 13/221,823

(22) Filed: Aug. 30, 2011

(65) Prior Publication Data

US 2012/0053608 A1 Mar. 1, 2012

(30) Foreign Application Priority Data

Aug. 30, 2010 (JP) ................................ 2010-192913
Jul. 27, 2011 (JP) ................................ 2011-164859

(51) Int. Cl.
*A61B 5/05* (2006.01)
*A61B 5/1486* (2006.01)
*A61B 5/145* (2006.01)
*A61B 5/00* (2006.01)

(52) U.S. Cl.
CPC ......... *A61B 5/14865* (2013.01); *A61B 5/14532* (2013.01); *A61B 5/6849* (2013.01)

(58) Field of Classification Search
None
See application file for complete search history.

(56) References Cited

U.S. PATENT DOCUMENTS

| | | | |
|---|---|---|---|
| 5,390,671 A | 2/1995 | Lord et al. | |
| 5,954,643 A * | 9/1999 | VanAntwerp et al. | 600/316 |
| 6,695,860 B1 * | 2/2004 | Ward et al. | 606/185 |
| 6,936,006 B2 * | 8/2005 | Sabra | 600/300 |
| 6,990,366 B2 | 1/2006 | Say et al. | |
| 7,660,615 B2 * | 2/2010 | VanAntwerp et al. | 600/316 |
| 7,905,833 B2 * | 3/2011 | Brister et al. | 600/309 |
| 8,025,658 B2 * | 9/2011 | Chong et al. | 604/890.1 |
| 2003/0225361 A1 * | 12/2003 | Sabra | 604/19 |
| 2006/0036144 A1 * | 2/2006 | Brister et al. | 600/345 |
| 2007/0027381 A1 * | 2/2007 | Stafford | 600/347 |
| 2007/0060814 A1 | 3/2007 | Stafford | |

(Continued)

FOREIGN PATENT DOCUMENTS

| | | |
|---|---|---|
| JP | 2002-503988 A | 2/2002 |
| JP | 2005-520648 A | 7/2005 |
| JP | 2008-506468 A | 3/2008 |
| WO | 89/11820 A1 | 12/1989 |
| WO | 2004/098683 A1 | 11/2004 |
| WO | 2006/017358 A1 | 2/2006 |

OTHER PUBLICATIONS

The Extended European Search Report dated Nov. 24, 2011; EP Application No. 11179352.7-1265.

*Primary Examiner* — Patricia Mallari
*Assistant Examiner* — Michael R Bloch
(74) *Attorney, Agent, or Firm* — Studebaker & Brackett PC

(57) ABSTRACT

The present invention provides a sensor insertion and removing device which is user-friendly and which does not cause infection. The sensor insertion and removing device has a sensor; a puncture blade member; a housing which houses the sensor and the puncture blade member; a guide part which is provided within the housing and which glidably supports the puncture blade member; a puncture blade operating part which inserts the sensor under the skin by causing the puncture blade member to glide along the guide part integrally with the sensor, upon delivering the puncture blade member outside the housing to puncture the skin, and which causes the puncture blade member to glide along the guide part in a state of being separated from the sensor, upon removing the puncture blade member from under the skin into the housing, and a sensor operating part which pulls out the sensor from under the skin and removes it from under the skin into the housing.

14 Claims, 28 Drawing Sheets

(56) References Cited

U.S. PATENT DOCUMENTS

| | | |
|---|---|---|
| 2007/0078320 A1 | 4/2007 | Stafford |
| 2007/0078321 A1 | 4/2007 | Mazza et al. |
| 2007/0078322 A1 | 4/2007 | Stafford |
| 2008/0009692 A1 | 1/2008 | Stafford |
| 2008/0064944 A1* | 3/2008 | VanAntwerp et al. ........ 600/373 |
| 2009/0234212 A1* | 9/2009 | Slomski et al. ............... 600/345 |
| 2010/0049014 A1* | 2/2010 | Funderburk et al. .......... 600/309 |
| 2010/0113897 A1* | 5/2010 | Brenneman et al. .......... 600/310 |
| 2010/0191082 A1* | 7/2010 | Brister et al. ................. 600/345 |
| 2011/0288574 A1* | 11/2011 | Curry et al. ................... 606/185 |

* cited by examiner

PUNCTURE ANGLE 40°

PUNCTURE ANGLE 60°

PUNCTURE ANGLE 90°

SENSOR INSERTION/RECOVERY DEVICE

This application claims the benefit of Japanese patent applications No. JP2010-192913 filed on Aug. 30, 2010 and No. JP2011-164859 filed on Jul. 27, 2011 in the Japanese Patent Office, the disclosure of which is herein incorporated in its entirety by reference.

TECHNICAL FIELD

The present invention relates to a sensor insertion and removing device.

BACKGROUND OF THE INVENTION

In recent years, various electrochemical sensors have been developed for usage such as the detection or quantitative determination of a specific component in the patient's bodily fluid such as blood. For example, known is a subcutaneous implant-type sensor which implants an electrochemical sensor under the patient's skin and continuously measures the target substance (specific component) contained in the specimen over a predetermined period of time. As an example of the subcutaneous implant-type sensor, there is a subcutaneous implant-type glucose sensor. With the subcutaneous implant-type glucose sensor, the specimen to be measured is the interstitial fluid, blood or the like existing outside the cells of the subcutaneous tissue. Moreover, a continuous glucose monitoring (CGM) device capable of continuously monitoring the glucose level by using this type of subcutaneous implant-type glucose sensor has also been developed.

As one mode of the subcutaneous implant-type sensor, there is a type comprising a sensor electrode formed on the tip side of a flexible, elongated sensor substrate based on the thin film masking technique, and a conductive contact pad formed on the base end side of the sensor substrate. This conductive contact pad is, for example, electrically connected to an appropriate measurement device according to a conventional method via an electrical wiring.

Normally, the base end side of the subcutaneous implant-type sensor to which the conductive contact pad is formed is disposed outside the body by being housed in a sensor housing (also referred to as a case or casing). Moreover, the sensor housing is attached to the skin, for example, by appropriate adhesive means such as an adhesive tape provided to the lower surface thereof. In addition, the tip side of the subcutaneous implant-type sensor where the sensor electrode is disposed penetrates the skin according to an appropriate method, and the sensor electrode formed on the tip side is percutaneously disposed under the skin. When the monitoring of the target substance is complete, the tip side of the sensor that is implanted under the skin is extracted outside the body.

Here, a user (for example, a patient or a physician) handling the subcutaneous implant-type sensor will demand user-friendliness of being able to easily insert (implant) the sensor under the skin. As related technology, for example, Patent document 1 discloses an insertion set for a percutaneous sensor, and Patent document 2 discloses a percutaneous specimen sensor assembly.

Patent document 1: Japanese Translation of PCT Application No. 2002-503988
Patent document 2: Japanese Translation of PCT Application No. 2008-506468
Patent document 3: Japanese Translation of PCT Application No. 2005-520648

With the foregoing conventional technologies, the tip side of the sensor to which the sensor electrode is formed is inserted under the skin together with an insertion needle. Subsequently, only the insertion needle is pulled outside the body in a state of disposing the sensor electrode at a predetermined position under the skin, and the measurement of the target substance is thereafter started. Nevertheless, with the insertion set described in Patent document 1, the insertion needle to which the patient's bodily fluid had adhered upon pulling the insertion needle outside the body is exposed to the outside. Thus, when a third party other than the patient such as the physician performs the operation of pulling out the insertion needle, the physician may come in contact with the patient's bodily fluid and get infected. Moreover, it is necessary to take separate measures for preventing the infection, and the handling of the subcutaneous implant-type sensor by the user becomes complicated, thereby deteriorating the user-friendliness.

Moreover, Patent document 2 discloses a component referred to as an applicator that enables the insertion of the sensor and needle. According to this applicator, the needle is not exposed to the outside upon pulling out the needle from under the skin. However, the applicator is a special component for inserting the subcutaneous implant-type sensor under the skin. Accordingly, in order to start the measurement, after removing the applicator from the mounting unit which serves as the housing, it is necessary to mount an electronic unit housing a sensor electronic device for processing the specimen data of the subcutaneous implant-type sensor on the mounting unit in place of the applicator. Accordingly, since the replacement of equipment is required during the insertion of the subcutaneous implant-type sensor and during the measurement of the target substance, it cannot be said that this is user friendly, and the probability of human error caused by the complication of the operation process will increase.

Moreover, in both of the foregoing conventional technologies, no special devisal is provided for improving the user-friendliness of users upon pulling out (extracting) the subcutaneous implant-type sensor from under the skin after the monitoring of the target substance is complete. In other words, the mode of the foregoing conventional technologies is to pull out the subcutaneous implant-type sensor from under the skin by removing the sensor housing while peeling the adhesive tape from the skin. Thus, when an inexperienced person attempts to pull out the subcutaneous implant-type sensor, there is a possibility that the user will suffer pain or the sensor will become damaged as a result of the strength of pulling out the sensor or the direction of applying the strength being unstable.

DISCLOSURE OF THE INVENTION

The present invention was devised in view of the foregoing circumstances. Thus, an object of this invention is to provide a sensor insertion and removing device which is user-friendly and which will not cause infection.

Means for Solving the Problems

In order to achieve the foregoing object, the present invention adopts the following means.

Specifically, the present invention is a sensor insertion and removing device including a sensor; a puncture blade member; a housing which houses the sensor and the puncture blade member; a guide part which is provided within the housing and which glidably (slidably) supports the puncture blade member; a puncture blade operating part which inserts the sensor under the skin by causing the puncture blade member to glide along the guide part integrally with the sensor, upon delivering the puncture blade member outside the housing to puncture the skin, and which causes the puncture blade member to glide along the guide part in a state of being separated from the sensor, upon removing the puncture blade member from under the skin into the housing, and a sensor operating part which pulls out the sensor from under the skin and removes it from under the skin into the housing.

According to the above, since the entire mechanism for inserting the sensor under the skin and removing the sensor is consolidated within the housing, it is possible to improve the user-friendliness of users. In particular, since the replacement of equipment or the like is not required before starting the monitoring of the target substance in the bodily fluid after the subcutaneous insertion of the sensor is complete, the user-friendliness is high, and the probability of human error by the user can also be reduced.

Moreover, the delivery of the puncture blade member and the sensor outside the housing and the removing thereof from under the skin into the housing can be performed via an adhesive surface opening formed at a part of the adhesive surface that is attached to the skin within the housing. According to the above, since the foregoing delivery and the removing are performed only via the adhesive surface opening that is not exposed to the outside once the housing is attached to the skin, the user will never come in contact with the puncture blade member and the sensor. Accordingly, upon removing the puncture blade member from under the skin into the housing after the sensor has been inserted under the skin, or upon removing the sensor from under the skin into the housing after the monitoring is complete, a third party such as a physician will not come in contact with the patient's bodily fluid, and there is no possibility of infection. In addition, since the puncture blade member is not exposed to the outside, the user will not get injured due to the puncture blade member or suffer any psychological discomfort. Thus, according to the present invention, it is possible to improve the user-friendliness and safety of users.

In the present invention, the puncture blade member may include a concave part for slidably receiving the sensor along a longitudinal direction of the puncture blade member. In the foregoing case, preferably, when the puncture blade operating part causes the puncture blade member to glide along the guide part integrally with the sensor, the sensor is maintained in a fitted state of being fitted in the concave part of the puncture blade member, and the fitted state is released when the puncture blade operating part causes the puncture blade member to glide along the guide part in a state of being separated from the sensor.

In the foregoing configuration, preferably, the depth of the concave part is set to be equal to or greater than the thickness of the sensor. According to the above, during the subcutaneous insertion of the sensor, it is possible to inhibit the sensor from getting hooked on subcutaneous tissue and becoming bent or otherwise damaged.

Moreover, an apical surface of the sensor may be inclined toward a base end side of the sensor from an exposed surface, which is on an opposite side to a contact surface which comes in contact with a bottom surface of the concave part, to the contact surface. According to the above, during the removing of the puncture blade member, the puncture blade member can be easily separated from the sensor.

Moreover, in the sensor insertion and removing device according to the present invention, an operation opening may be formed in the housing, the puncture blade operating part may include a first grip part which is fixed to a predetermined first basic portion in the puncture blade member, and inserted through the operation opening so as to be exposed outside the housing, the sensor operating part may include a second grip part which is fixed to a predetermined second basic portion in the sensor, and inserted through the operation opening so as to be exposed outside the housing, the gliding operation of the puncture blade member may be performed in conjunction with the operation of the first grip part, and the removing operation of the sensor may be performed in conjunction with the operation of the second grip part. In the foregoing case, for example, the guide part may include a linear guide part which is formed linearly, and the operation opening in the housing is formed linearly so as to oppose the linear guide part, the gliding operation of the puncture blade member may be performed in conjunction with the sliding operation of the first grip part through (in) the operation opening, and the removing operation of the sensor may be performed in conjunction with the sliding operation of the second grip part through (in) the operation opening.

Otherwise, the guide part may include an arc-shaped guide part which is formed in an arc shape, the gliding operation of the puncture blade member may be performed in conjunction with the rotational operation of the first grip part, and the removing operation of the sensor may be performed in conjunction with the rotational operation of the second grip part.

As a result of adopting the foregoing so-called slide mechanism or winding mechanism, the subcutaneous insertion and removing of the sensor can be performed suitably.

Moreover, the puncture blade operating part and the sensor operating part may be respectively formed with contact parts which mutually come in contact only during the operation, by the puncture blade operating part, of delivering the puncture blade member outside the housing. Moreover, a first restricting part which restricts the operation, by the puncture blade operating part, of delivering the puncture blade member outside the housing may be further provided, and the first restricting part may be provided so that the sensor reaches a predetermined target insertion depth at a point in time when restriction by the first restricting part is started. According to the above, the sensor (for instance, the electrode part provided at the tip side of the sensor) can be inserted to the target insertion depth in just proportion.

Furthermore, in the present invention, the sensor operating part may further include a locking pin which is biased toward an inner wall surface of the housing by an elastic member, and the inner wall surface of the housing may be provided with a locking hole to which the locking pin is fitted at a point in time when restriction by the first restricting part is started. According to the above, upon removing the puncture blade member from under the skin into the housing after completing the subcutaneous insertion of the sensor, it is possible to inhibit the sensor from following the removing operation of the puncture blade member, and inhibit the sensor insertion depth from deviating from the target insertion depth.

Moreover, in the present invention, the guide part may be axially supported in a swingable manner relative to the housing, and the sensor insertion and removing device may further a comprise puncture angle adjustment unit which adjusts the puncture angle of the puncture blade member by changing the swing stop position of the guide part relative to the housing. According to the above, it is possible to achieve a balance between the reliability of the measurement results of the target substance and the alleviation of pain during the puncture of the puncture blade member.

Moreover, the present invention may also be viewed as a sensor insertion and removing method. Specifically, the present invention is a sensor insertion and removing method comprising a setup step of setting, on skin, a housing which houses a sensor and a puncture blade member and which is internally provided with a guide part for glidably supporting the puncture blade member, a sensor insertion step of inserting, after the setup step, the sensor under the skin by causing the puncture blade member to glide along the guide part integrally with the sensor upon delivering the puncture blade member outside the housing to puncture the skin, a puncture blade removing step of removing, after the sensor insertion step, the puncture blade member from under the skin into the housing by causing the puncture blade member to glide along the guide part in a state of being separated from the sensor, and a sensor removing step of removing, after the puncture blade removing step, the sensor from under the skin into the housing by pulling it out from under the skin.

Moreover, with the sensor insertion and removing method of the present invention, the puncture blade member may include a concave part for slidably receiving the sensor along a longitudinal direction of the puncture blade member, in the sensor insertion step, the sensor may be maintained in a fitted state of being fitted in the concave part of the puncture blade member, and, in the puncture blade removing step, the fitted state may be released.

Moreover, with the sensor insertion and removing method of the present invention, an operation opening may be formed in the housing, a first grip part may be fixed to a predetermined first basic portion in the puncture blade member, and the first grip part may be inserted through the operation opening so as to be exposed outside the housing, a second grip part may be fixed to a predetermined second basic portion in the sensor, and the second grip part may be inserted through the operation opening so as to be exposed outside the housing, the gliding operation of the puncture blade member in the sensor insertion step and puncture blade removing step may be performed in conjunction with the operation of the first grip part, and the removing operation of the sensor in the sensor removing step may be performed in conjunction with the operation of the second grip part.

Moreover, with the sensor insertion and removing method of the present invention, the guide part may be axially supported in a swingable manner relative to the housing, and the sensor insertion and removing method may further include a puncture angle adjustment step of adjusting the puncture angle of the puncture blade member by changing the swing stop position of the guide part relative to the housing before the sensor insertion step.

Effects of the Invention

According to the present invention, it is possible to provide a sensor insertion and removing device that is user-friendly and which will not cause infection.

DETAILED DESCRIPTION OF THE INVENTION

A sensor insertion and removing device, a monitoring system comprising the same, and a method of inserting and removing a sensor according to the embodiments of the present invention are now explained with reference to the appended drawings. The configurations described in the following examples are merely exemplifications, and the sensor insertion and removing device and method according to these embodiments are not limited to the configurations and methods of the embodiments shown below. For example, the size, material, shape and relative arrangement of the components in the respective embodiments are not intended to limit the technical scope of the invention only thereto.

Embodiment 1

Figure 1:
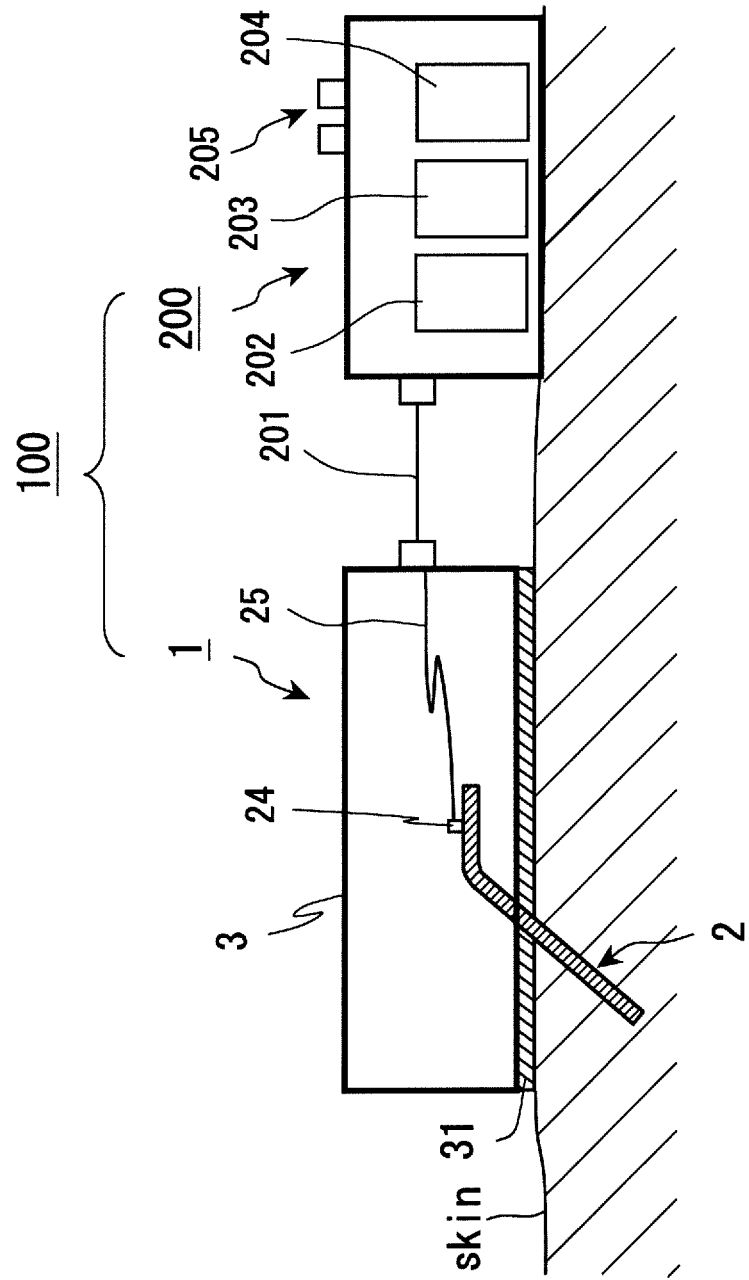
FIG. 1 is an overall configuration diagram of the monitoring device according to Embodiment 1.

The first embodiment of the sensor insertion and removing device and the monitoring system according to this embodiment are now explained. FIG. 1 is the overall configuration diagram of the monitoring system 100 according to the first embodiment. The monitoring system 100 is configured from a sensor insertion and removing device 1 which houses an electrochemical sensor (hereinafter simply referred to as the "sensor") 2 for generating a sensor signal (response current value) according to the concentration of the target component in the specimen, and a control unit 200 which receives the sensor signal from the sensor 2, computes the concentration of the target component in the specimen, and sends the computation result to an external device.

Figure 2:
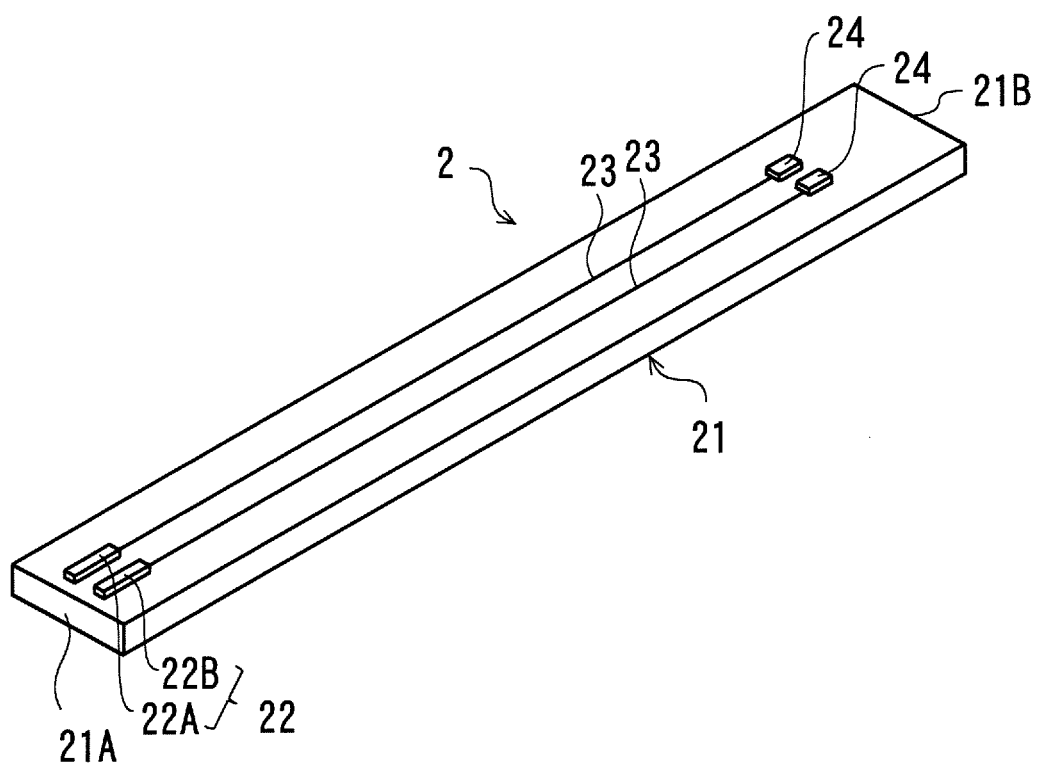
FIG. 2 is an overall perspective view of the sensor according to Embodiment 1.

FIG. 2 is an overall perspective view of the sensor 2 according to the first embodiment. The sensor 2 is a subcutaneous implant-type electrochemical sensor which is used by its front end side being implanted under the patient's skin. In this embodiment, a case is explained where this sensor is used as a glucose sensor for measuring the glucose concentration (that is, the blood glucose level) contained in bodily fluids such as the interstitial fluid and blood existing outside the cells of the patient's subcutaneous tissue, but the present invention is not limited thereto.

The sensor 2 includes a sensor substrate 21, a sensor electrode 22, a lead wire 23, and a connector 24. The sensor substrate 21 is flexible, and is a so-called flexible thin film sensor. In addition, the sensor substrate 21 can be favorably formed from a material possessing biocompatibility and insulation properties. For example, as the sensor substrate 21, used may be resin of polypropylene, polyimide, polyethylene terephthalate, polyether ether ketone, polyethylene naphthalate, and so on.

The sensor substrate 21 has an elongated shape as shown in the drawings, and a sensor electrode 22 is provided at its front end part 21A. Two sensor electrodes 22 are provided adjacently in the width direction of the sensor substrate 21, and one is a working electrode 22A while the other is a counter electrode 22B. The sensor electrode 22 can be formed, for example, by vapor deposition, sputtering, printing (screen printing, gravure printing), transfer printing or other methods. The working electrode 22A is the part that performs electron transfer with glucose as the target component in the bodily fluid. The counter electrode 22B is the electrode that is used for applying voltage together with the working electrode 22A. One end of a lead wire 23 is connected to the working electrode 22A and the counter electrode 22B. In addition, the other end of the lead wire 23 is connected to the connector 24 provided to the base end part 21B of the sensor substrate 21.

A reagent enzyme is formed on the surface of the working electrode 22A. As this reagent enzyme, for example, glucose oxidase (GOD), glucose dehydrogenase (GDH) and the like can be suitably used. As a method of immobilizing the reagent enzyme, various known methods of using polymerizable gel, macromolecules such as polyacrylamide or phosphorus, MPC polymer obtained by introducing a silane coupling agent into phospholipid polymer, or protein film can be used. Note that, in a manner of covering the sensor electrode 22, the sensor substrate 21 may also be covered with an outer layer film (not shown) which allows the permeation (infiltration) of the interstitial fluid or blood as the specimen. This type of outer layer film also functions as a protective layer for protecting the sensor electrode 22.

The sensor 2 forwards the generated sensor signal to the control unit 200 via the connector 24, a cable 25, and a cable connector 201. The control unit 200 is provided with a power source 202, a controller 203, a transmitter 204, and an operation button 205. The controller 203 is an electronic control unit for controlling the operational status of the control unit 200 and the sensor 2 according to the state of the operation button 205. The controller 203 comprises a ROM, a RAM and the like which store various programs in addition to a CPU, and computes the glucose concentration based on the sensor signal input from the sensor 2.

The power source 202 is a device for supplying control power to the sensor 2, and applies voltage to the sensor electrode 22 based on a command from the controller 203. When voltage is applied between the sensor electrodes 22, electrons are transferred between the glucose contained in the bodily fluid and the working electrode 22A. The sensor 2 outputs the obtained response current value as a sensor signal to the controller 203, and the controller 203 computes the blood glucose level based on the sensor signal acquired from the sensor 2. The controller 203 sends the computation result of the blood glucose level (glucose concentration), as needed, from the transmitter 204 to an external information processing terminal (for example, a personal computer).

The sensor 2 is maintained in a state of being indwelled under the skin from the start of monitoring the glucose concentration until the lapse of a predetermined monitoring period (for instance, roughly several days to several weeks). Note that the control program of the controller 203 is set, for example, to perform measurement processing of the glucose concentration at predetermined intervals during the monitoring period. In addition, the control unit 200 may also be provided with a monitor for displaying the computation result of the glucose concentration, and a warning means for emitting a warning sound if the computed blood glucose level shows an abnormal value.

Figure 3:
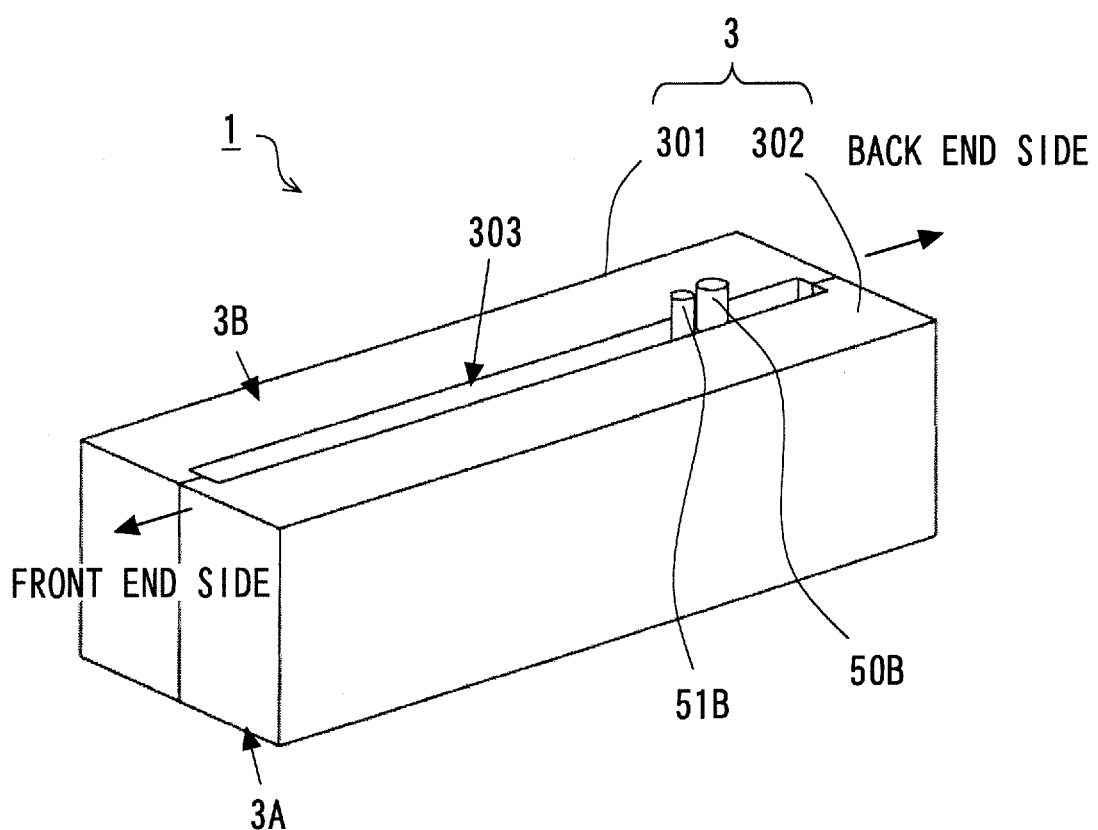
FIG. 3 is an external perspective view of the sensor insertion and removing device according to Embodiment 1.

The sensor insertion and removing device 1 according to this embodiment is now explained in detail. FIG. 3 is an outer perspective view of the sensor insertion and removing device 1 according to the first embodiment. The sensor insertion and removing device 1 comprises a housing 3 as a case which houses the sensor 2, the puncture sheet blade 4 and the like.

An adhesive tape 31 (shown in FIG. 1 but omitted in FIG. 3) is affixed to the under surface 3A of the housing 3, and the housing 3 is fixed to the abdomen, arm or the like of the patient by the adhesive tape 31. Thus, the under surface 3A of the housing 3 can also be referred to as the adhesive surface to be attached to the skin. Note that the foregoing control unit 100 may also be mounted on the skin with a fixing means such as an adhesive tape as with the housing 3, or be mounted on the patient's belt or belt loop via a hook or the like.

The housing 3 is configured from a first case 301 and a second case 302. The shape of the cross section of the first case 301 and the second case 302 that is parallel to the upper surface 3B and the under surface 3A is a substantial U-shape. In addition, as a result of the first case 301 and the second case 302 being mutually coupled as shown in the diagram, a housing space is formed therein, and an opening 303 that is in communication with such housing space is formed on the upper surface 3B. As shown in the diagram, the opening 303 formed on the upper surface 3B is provided as an elongated linear shape, and a sheet blade knob 50B (first grip part) and a sensor knob 51B (second grip part) are slidably inserted along the longitudinal direction of the opening 303. In the ensuing explanation, the opening 303 is referred to as the "slide opening". In this embodiment, the slide opening 303 corresponds to the operation opening of the present invention.

Figure 4:
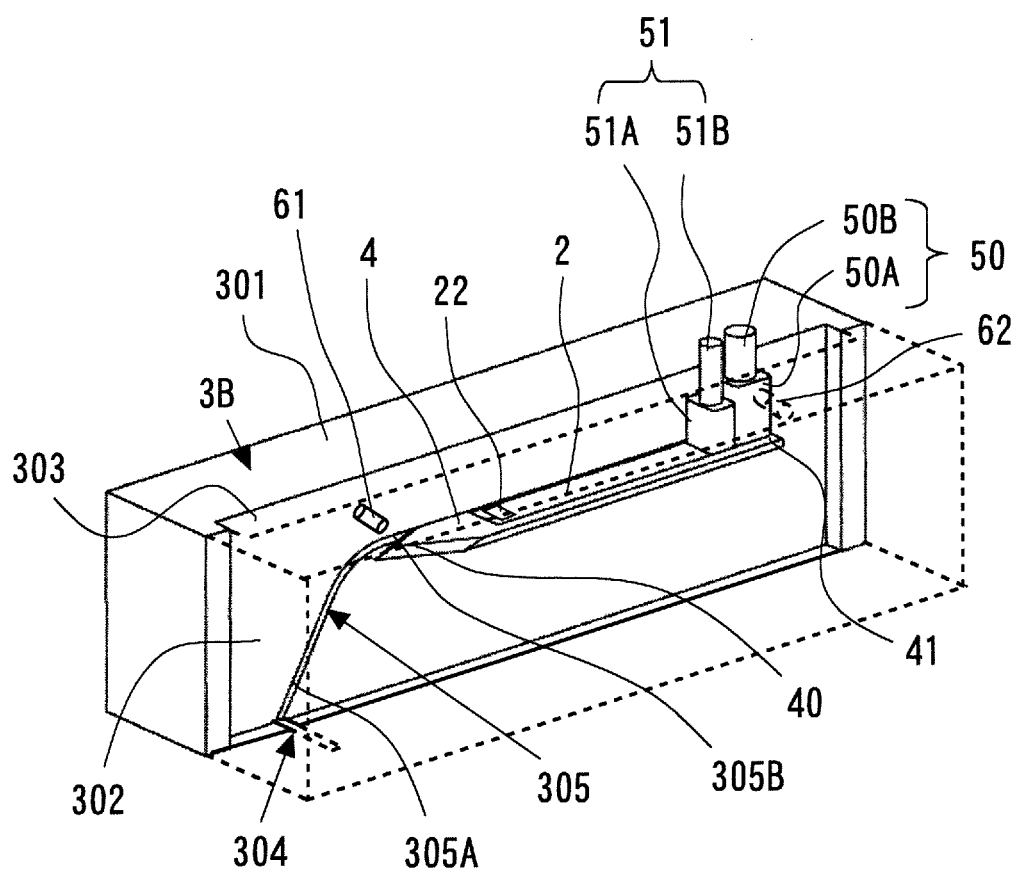
FIG. 4 is an explanatory diagram explaining the internal structure of the housing of the sensor insertion and removing device according to Embodiment 1.

FIG. 4 is an explanatory diagram explaining the internal structure of the housing 3, and the second case 302 side is shown with a broken line for the sake of convenience. A lower surface opening 304 provided to the under surface 3A of the housing 3. Note that the under surface 3A of the housing 3 can also be referred to as the adhesive surface to be attached to the skin. The lower surface opening 304 is an opening that is used for delivering the puncture sheet blade 4 and the sensor 2 housed in the housing 3 toward the skin, or individually removing the puncture sheet blade 4 and the sensor 2 indwelled under the skin back into the housing 3. The lower surface opening 304 includes an effective cross section area of a level that allows the smooth passage of the puncture sheet blade 4 that received the sensor 2. In the illustrated example, the lower surface opening 304 is of a rectangular shape, but other shapes may also be adopted.

A guide groove 305 as a guide part is formed inside the housing 3 in a manner of being in communication with the lower surface opening 304. As shown in the diagram, one guide groove 305 is configured as a result of a groove provided to the first case 301 side and a groove provided to the second case 302 side being combined. In this diagram, the guide groove 305 is configured as an elongated groove having a rectangular cross section. The guide groove 305 is a guide member that glidably (or slidably, hereinafter the same in this specification) supports the puncture sheet blade 4. The guide groove 305 and the slide opening 303 are formed so that they mutually overlap vertically. The vertical relation referred to herein is based on a case of hypothesizing that the upper surface 3B and the under surface 3A of the housing 3 are horizontal planes.

The puncture sheet blade 4 (puncture blade member) is a sheet blade in which its blade edge part 40 at the front end side is sharpened and pointed, and can be prepared, for example, with medical grade stainless steel or the like. The puncture sheet blade 4 punctures the skin upon inserting the sensor 2 under the skin. Moreover, the thickness of the puncture sheet blade 4 is defined so that a certain level of flexibility can be expected to prevent damage such as breaking when it is slid along the guide groove 305.

A sheet blade holder 50 as a puncture blade operating part is fixed integrally with the puncture sheet blade 4 to the back end part 41 (first basic portion) of the puncture sheet blade 4. The sheet blade holder 50 is configured from a first joint part 50A to be bonded to the back end part 41 of the puncture sheet blade 4, and a sheet blade knob 50B that is formed on the first joint part 50A. In this embodiment, the first joint part 50A has a quadrangular prism shape and the sheet blade knob 50B has a cylindrical shape, but they are not limited to the combination of these shapes. Moreover, the diameter of the sheet blade knob 50B is set to be slightly smaller than the width of the slide opening 303, and the sheet blade knob 50B is inserted into the slide opening 303 so that is upper part is exposed to the outside of the housing 3.

Figure 5:
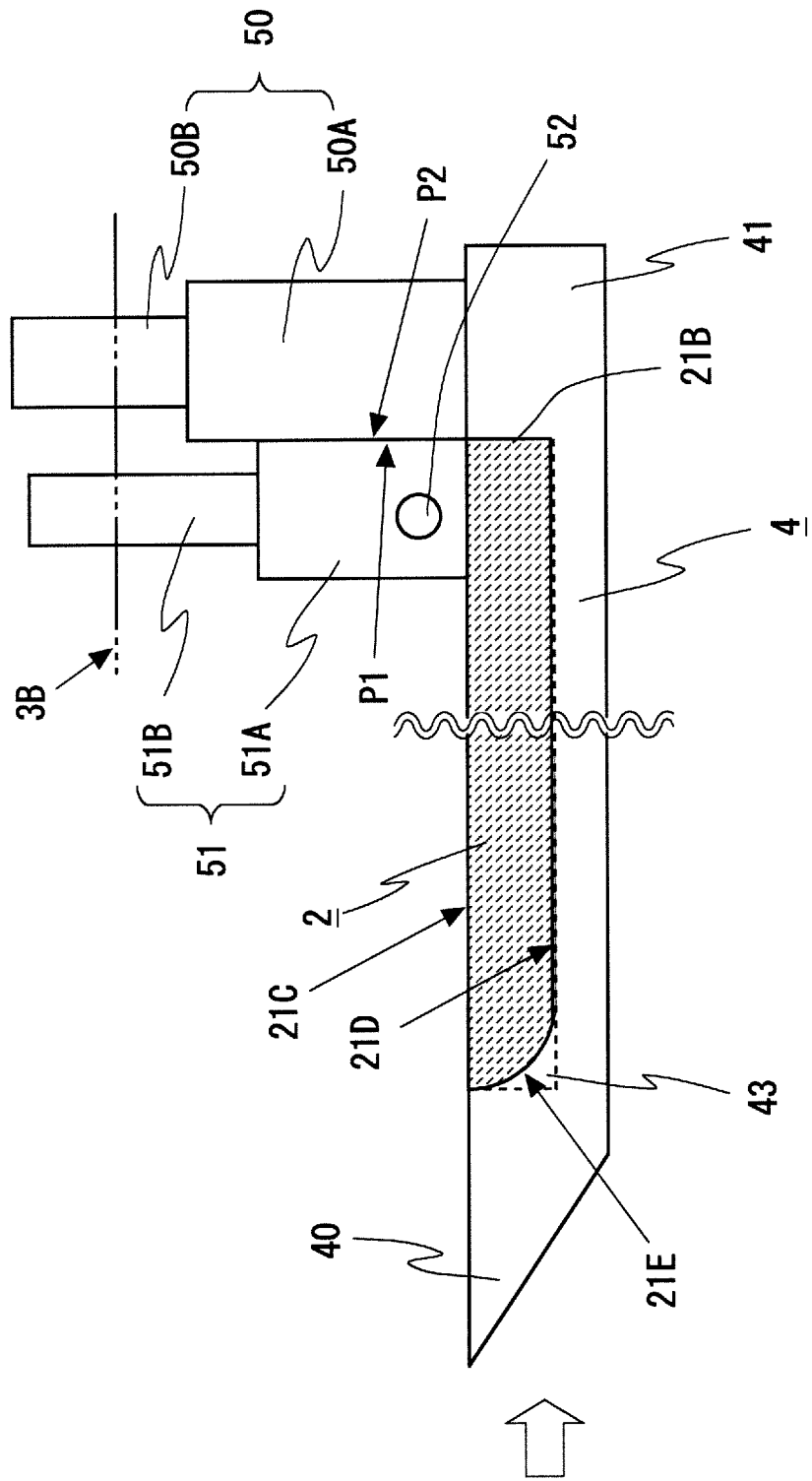
FIG. 5 is an explanatory diagram explaining the received state of the sensor relative to the puncture sheet blade.

FIG. 5 is an explanatory diagram explaining the state that the sensor 2 is received by the puncture sheet blade 4. As shown in the diagram, a long groove 43 (concave part) for slidably receiving the sensor 2 is provided on the puncture sheet blade 4 along the longitudinal direction of the puncture sheet blade 4. The width of the long groove 43 and the length of the longitudinal direction are set to be equal to or slightly greater than the width and length of the sensor 2. In particular, by setting the depth of the long groove 43 to be greater than the thickness of the sensor 2, the sensor 2 is prevented from protruding from the long groove 43 when viewed from the direction of the outlined arrow shown in the diagram.

In the sensor substrate 21, the surface where the sensor electrode 22 is formed is referred to as an "electrode forming surface 21C" and the surface opposite thereto is referred to as a "rear surface 21D". The long groove 43 is configured to receive the sensor 2 so that the rear surface 21D of the sensor substrate 21 comes in contact with the bottom surface 43A of the long groove 43 and the electrode forming surface 21C is exposed from the open surface of the long groove 43. Moreover, a tapered part 21E in which its apical surface is inclined obliquely is formed on the front end part 21A of the sensor 2. The tapered part 21E is inclined from the electrode forming surface 21C (exposed surface), which is on the side that is opposite to the rear surface 21D where the apical surface of the sensor substrate 21 comes in contact with the bottom surface 43A of the long groove 43, to the rear surface 21D (contact surface) toward the base end part 21B. Note that, in FIG. 1 and FIG. 2, the illustration of the tapered part 21E is omitted. The tapered part 21E may also be configured as an inclined flat surface in substitute of being formed as a curved surface shape as shown in FIG. 5.

As shown in FIG. 5, a sensor holder 51 as a sensor operating part in the present invention is fixed, integrally with the sensor substrate 21 of the sensor 2, to the base end part 21B (second basic portion) of the electrode forming surface 21C of the sensor 2. The sensor holder 51 is configured from a second joint part 51A to be bonded on to the base end part 21B of the sensor 2, and a sensor knob 51B formed on the second joint part 51A. In the sensor holder 51 also, the second joint part 51A has a quadrangular prism shape and the sensor knob 51B has a cylindrical shape, but they are not limited to the combination of these shapes. Moreover, the diameter of the sensor knob 51B is set to be smaller than the width of the slide opening 303, and the upper part of the sensor knob 51B is inserted through the slide opening 303 so as to be exposed to outside from the slide opening 303. In addition, as shown in FIG. 4, the sheet blade knob 50B and the sensor knob 51B are arranged alongside along the longitudinal direction of the slide opening 303.

The guide groove 305 is now explained in detail. As shown in FIG. 4, the guide groove 305 is configured from a puncture angle defining guide groove 305A and a slide guide groove 305B (linear guide part). The puncture angle defining guide groove 305A is connected to the lower surface opening 304 formed on the under surface 3A of the housing 3, and is disposed at an inclination relative to the under surface 3A of the housing 3. The slide guide groove 305B is formed linearly so that it becomes parallel to the upper surface 3B of the housing 3 to which the slide opening 303 is formed. In relation to the guide groove 305, the end that is closer to the lower surface opening 304 is defined as the "front end" and the end that is father from the lower surface opening 304 is defined as the "back end". The guide groove 305 is disposed, from its front end side, in the order of a puncture angle defining guide groove 305A and a slide guide groove 305B, and the two are loosely connected. Note that the assembly of the first case 301 and the second case 302 is performed in a state where both side surfaces of the puncture sheet blade 4 are fitted into the guide groove 305.

The sensor insertion and removing device 1 is in the state shown in FIG. 3 and FIG. 4 in the initial state prior to be set on the skin. The sensor 2 becomes a received state by being fitted into the long groove 43 of the puncture sheet blade 4. The position of the sheet blade knob 50B and the sensor knob 51B in the initial state is disposed on the back end side in the longitudinal direction of the slide opening 303 so that the back end part 41 of the puncture sheet blade 4 bonded to the sheet blade holder 50 is positioned at the back end side of the guide groove 305 (refer to FIG. 4). Moreover, as described in detail later, when the user is to use the sensor insertion and removing device 1, the user slides the sheet blade knob 50B and the sensor knob 51B along the longitudinal direction of the slide opening 303. Thus, the slide opening 303 is favorably formed on a surface other than the under surface 3A to be fixed to the skin and a surface through which the virtual axis of the slide guide groove 305B does not penetrate. In this embodiment, the slide opening 303 is provided to the upper surface 3B of the housing 3 as an example of such a surface.

Figure 6:
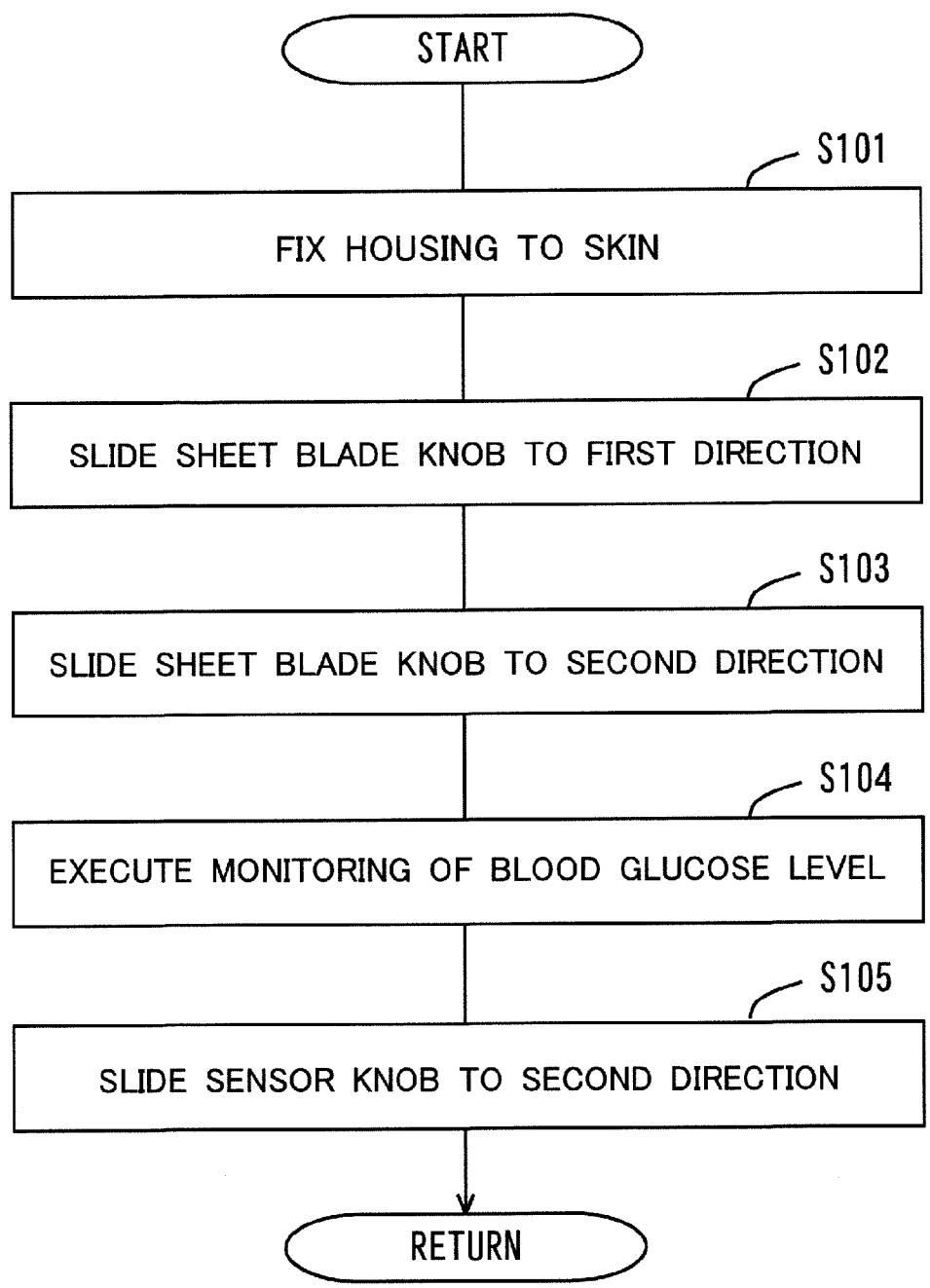
FIG. 6 is a flowchart showing the procedure for using the sensor insertion and removing device according to Embodiment 1.

The operation of the sensor insertion and removing device 1 is now explained. The sensor insertion and removing device 1 is used for implanting the sensor 2 percutaneously under the skin upon monitoring the target component with the monitoring system 100, and removing the used sensor 2 from the housing 3 once again after the completion of the monitoring period. FIG. 6 is a flowchart showing the procedures upon using the sensor insertion and removing device 1. The method of inserting and removing the sensor 2 (insertion and removing method) is described as a partial step described in the flowchart.

Foremost, the user peels the release film (not shown) of the adhesive tape 31 which is attached to the under surface 3A of the housing 3, and disposes the housing 3 at a predetermined position on the skin. Subsequently, by lightly pressing the housing 3 against the skin, the housing 3 is fixed to the skin (step S101: setup step). In this state, the sensor insertion and removing device 1 is in the initial state shown in FIGS. 3 and 4. In the initial state, as shown in FIG. 5, a first contact surface P1 in the first joint part 50A of the sheet blade holder 50 and a second contact surface P2 in the second joint part 51A of the sensor holder 51 are in mutual contact.

Subsequently, the user grips the sheet blade knob 50B of the sheet blade holder 50 and slides it along the longitudinal direction of the slide opening 303 in a direction from the back end side toward the front end side (this direction is hereinafter referred to as the "first direction") (step S102: sensor insertion step). Consequently, in coordination with the slide operation of the sheet blade knob 50B, the puncture sheet blade 4 causes the guide groove 305 to slide from the back end side toward the front end side. Here, since the second contact surface P2 on the sensor holder 51 (second joint part 51A) side is pressed by the first contact surface P1 on the sheet blade holder 50 (first joint part 50A) side, the sensor 2 that is in a state of being received by the long groove 43 of the puncture sheet blade 4 is also operated passively. As a result, the puncture sheet blade 4 can be caused to slide (glide) toward the front end side of the guide groove 305 integrally with the sensor 2.

When the blade edge part 40 of the puncture sheet blade 4 is delivered from the lower surface opening 304 toward the skin, the puncture sheet blade 4 punctures the skin and the sensor 2 that is fitted in the long groove 43 of the puncture sheet blade 4 is also implanted under the skin. As explained with reference to FIG. 5, since the sensor 2 is protruding from the long groove 43 in its thickness direction, the sensor 2 will not be bent as a result of the sensor 2 getting stuck on a subcutaneous tissue or the like during the insertion of the sensor 2. Moreover, the puncture angle of the puncture sheet blade 4 relative to the skin is decided based on the angle that is formed by the puncture angle defining guide groove 305A and the under surface 3A of the housing 3. Thus, in this embodiment, the angle formed by the puncture angle defining guide groove 305A and the under surface 3A is adjusted in advance so that the puncture angle of the puncture sheet blade 4 becomes a predetermined target puncture angle.

As shown in FIG. 4, a first slide restricting part 61 and a second slide restricting part 62 are provided to the side surface inside the housing 3. These restricting parts 61, 62 are members for defining and adjusting the movable range upon sliding the sensor knob 51B and the sheet blade knob 50B. When the user grips the sheet blade knob 50B and slides it in the first direction, it comes in contact with the second joint part 51A of the sensor holder 51 (more specifically, the surface on the side that is opposite to the second contact surface P2 in the second joint part 51A), and restricts any further slide operation of the sensor knob 51B toward the first direction. Consequently, the second contact surface P2 on the sensor holder 51 side and the first contact surface P1 on the sheet blade holder 50 side interfere with each other, and the slide operation of the sheet blade knob 50B in the first direction is thereby restricted. As a result, the puncture sheet blade 4 can no longer be delivered from the housing 3, and the blade edge part 40 will no longer slide deeper into the skin.

Thus, in this embodiment, the first slide restricting part 61 is disposed so that the sensor electrode 22 of the sensor 2 just reaches the target insertion depth at the time that the restriction of the sheet blade knob 50B in the first direction by the first slide restricting part 61 is started; that is, the time that the sensor knob 51B comes in contact with the first slide restricting part 61. Consequently, the user can reliably cause the sensor electrode 22 to reach the target insertion depth by sliding the sheet blade knob 50B until its movement is restricted by the first slide restricting part 61.

Figure 7:
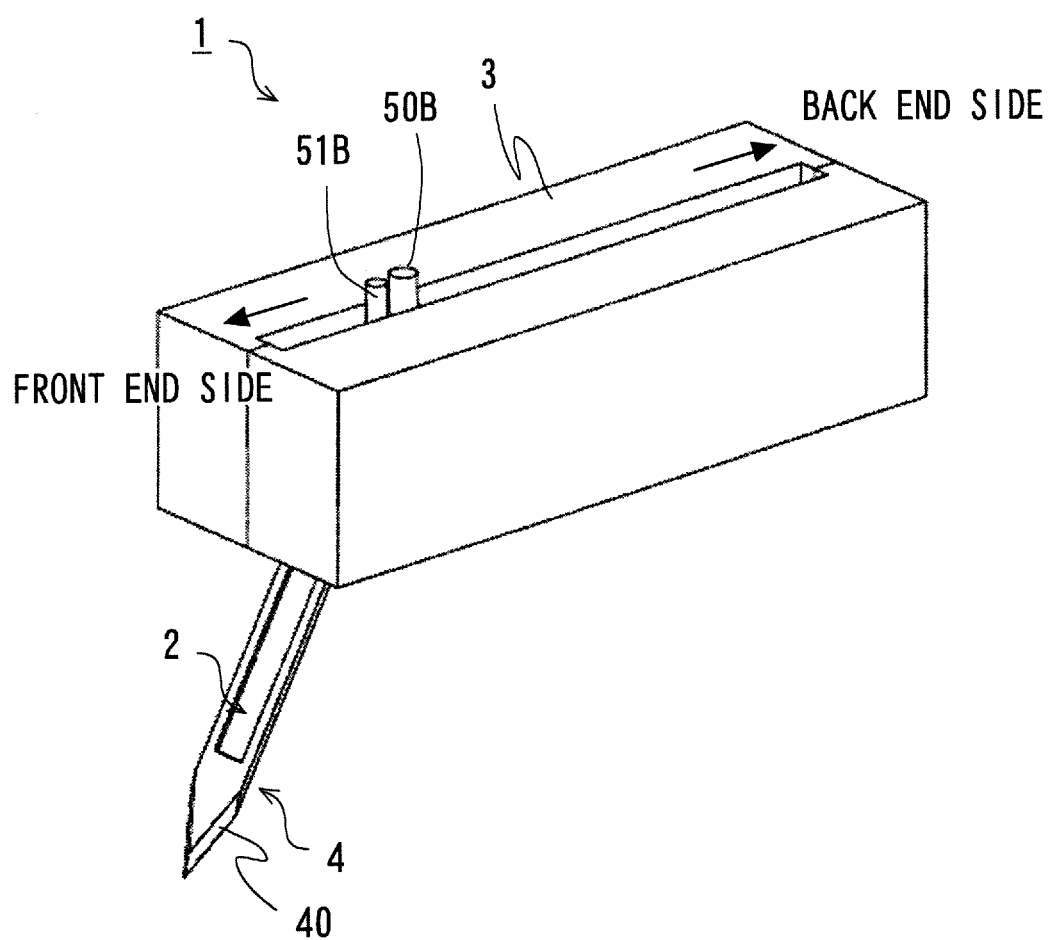
FIG. 7 is a diagram showing a state where the puncture of the puncture sheet blade is complete in the sensor insertion and removing device according to Embodiment 1.

FIG. 7 shows a state where the puncture by the puncture sheet blade 4 is complete. In this state, the sensor electrode 22 of the sensor 2 is disposed at a predetermined target insertion depth. Note that, in this embodiment, the slide operation of the sheet blade holder 50 is indirectly restricted in the first direction as a result of causing the first slide restricting part 61 to come in contact with the sensor holder 51, but the configuration may also be such that the slide operation of the sheet blade holder 50 is directly restricted. For example, the first slide restricting part 61 may be disposed at a position where the sensor electrode 22 comes in contact with the sheet blade holder 50 at a timing of reaching the target insertion depth.

Figure 8A:
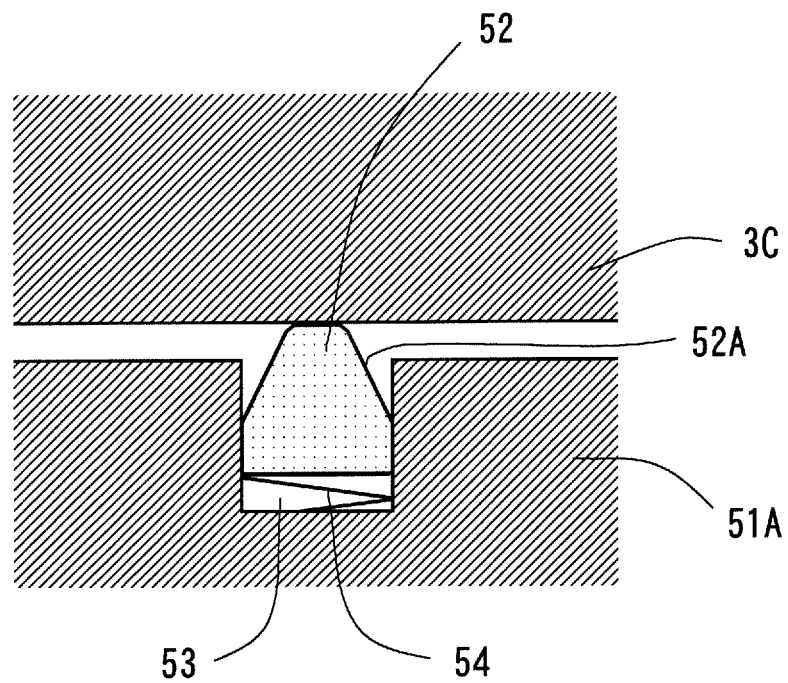
FIG. 8A is a diagram showing the relationship of the locking pin and the locking hole upon sliding the sheet blade knob in the first direction, and is a diagram showing a state before the sensor knob comes in contact with the first slide restricting part.
Figure 8B:
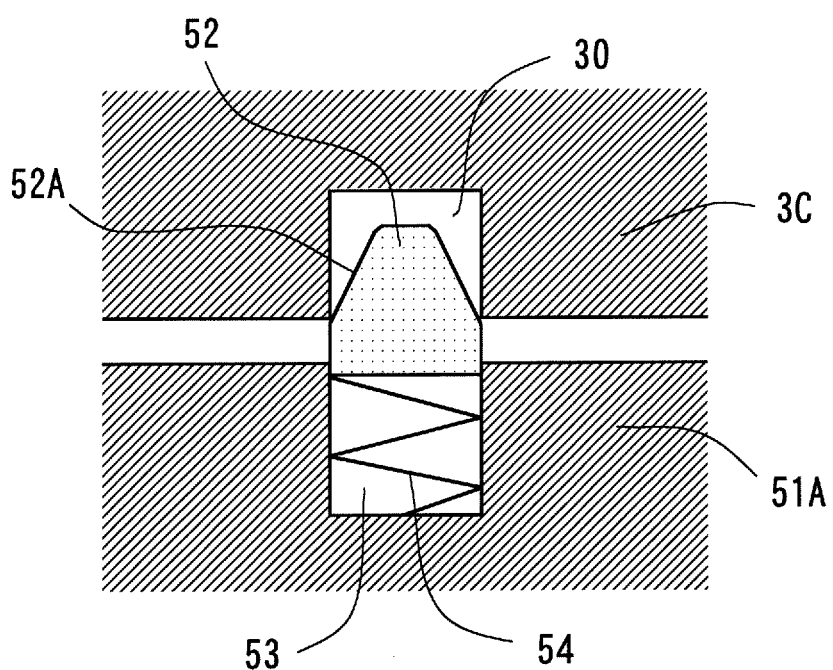
FIG. 8B is a diagram showing the relationship of the locking pin and the locking hole upon sliding the sheet blade knob in the first direction, and is a diagram showing a state at a point in time when the sensor knob comes in contact with the first slide restricting part.

Moreover, as shown in FIG. 5, a locking pin 52 that is biased toward the inner wall surface of the housing 3 is formed on the side surface of the second joint part 51A of the sensor holder 51 (surface that is orthogonal to the second contact surface P2). More specifically, as shown in FIGS. 8A and 8B, a housing concave part 53 for housing the locking pin 52 is formed on the side surface of the second joint part 51A, and the bottom surfaces of the housing concave part 53 and the locking pin 52 are bonded via a spring member 54 (elastic member). FIG. 8A shows the state before the sensor knob 51B comes in contact with the first slide restricting part 61 upon sliding the sheet blade knob 50B in the first direction, and FIG. 8B shows the state at the time that the sensor knob 51B just comes in contact with the first slide restricting part 61.

As shown in FIG. 8A, before the sensor knob 51B comes in contact with the first slide restricting part 61, the locking pin 52 is housed in the concave part 53 as a result of the locking pin 52 being pressed against the inner wall surface 3C of the housing 3. Accordingly, the sensor holder 51 slides while following the movement of the sheet blade holder 50 while causing the apex of the locking pin 52 to be in slidable contact with the inner wall surface 3C. Moreover, a locking hole 30 which is fitted with the locking pin 52 is provided to a position where the locking pin 52 is placed opposite to the inner wall surface 3C of the housing 3 at the time that the sensor knob 51B comes in contact with the first slide restricting part 61 (refer to FIG. 8B). Thus, the locking pin 52 is locked with the locking hole 30 at the timing that the sheet blade knob 50B comes in contact with the first slide restricting part 61.

Subsequently, the user grips the sheet blade knob 50B of the sheet blade holder 50, and slides it in a direction that is opposite to the first direction (hereinafter referred to as the "second direction") along the longitudinal direction of the slide opening 303 (step S103: puncture blade removing step). Here, since the locking pin 52 is locked with the locking hole 30, the fitted state of the sensor 2 in the long groove 43 of the puncture sheet blade 4 is released as a result of the sheet blade holder 50 sliding in a direction that breaks away from the sensor holder 51.

In particular, as shown in FIG. 5, since a tapered part 21E is formed on the apical surface of the sensor 2, when the user slides the sheet blade knob 50B in the second direction; that is, in a direction where the first contact surface P1 of the sheet blade holder 50 breaks away from the second contact surface P2 of the sensor holder 51, the tapered part 21E in the sensor 2 can more easily run onto the edge of the long groove 43. Accordingly, the sensor 2 can be easily separated from the long groove 43 by causing it to slide against the long groove 43 of the puncture sheet blade 4.

Figure 9:
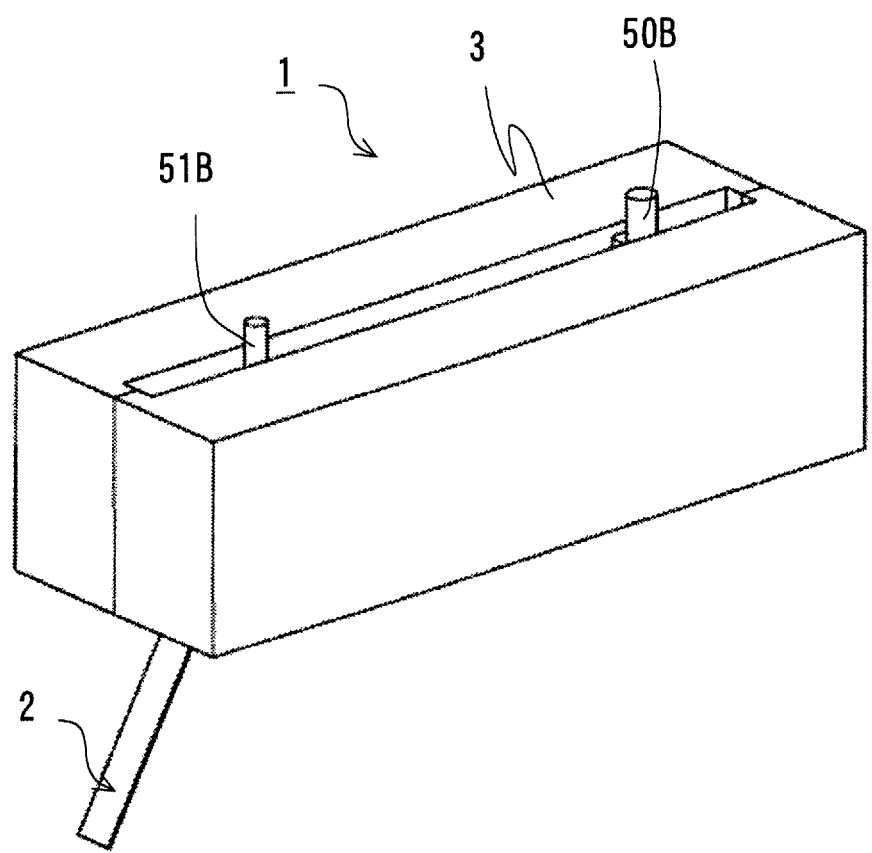
FIG. 9 is a diagram showing a state where the removing of the puncture sheet blade is complete in the sensor insertion and removing device according to Embodiment 1.

Consequently, the puncture sheet blade 4 slides along the guide groove 305 toward the back end side of the guide groove 305 in a state where the puncture sheet blade 4 is separated from the sensor 2, and only the puncture sheet blade 4 is removed from under the skin in a state where the sensor 2 is implanted under the skin. Here, the sensor 2 is prevented from following the puncture sheet blade 4 and being removed based on the operation of the locking pin 52 formed on the sensor holder 51 and the tapered part 21E formed on the apical surface of the sensor 2. Thus, the insertion depth of the sensor electrode 22 will not deviate from the target insertion depth. FIG. 9 is a diagram showing the state where the removing of the puncture sheet blade 4 is complete. In other words, in this state, the blade edge part 40 is returned via the lower surface opening 304 to the inside of the housing 3, and only the sensor 2 is implanted under the skin.

Note that, in step S103, when the sheet blade knob 50B is caused to slide in the second direction, the second slide restricting part 62 shown in FIG. 4 will ultimately come in contact with the first joint part 50A of the sheet blade holder 50 (more specifically, the surface on the side that is opposite to the first contact surface P1 in the first joint part 50A). At this point in time, the slide operation of the sensor knob 51B in the second direction is restricted, and the sliding of the puncture sheet blade 4 toward the back end side of the guide groove 305 will also stop. Thus, the position that the second slide restricting part 62 is disposed is adjusted so that the blade edge part 40 of the puncture sheet blade 4 is completely housed in the housing 3 at the time that the second slide restricting part 62 comes in contact with the first joint part 50A of the sheet blade holder 50.

The slidable range of the sensor knob 51B and the sheet blade knob 50B can be restricted by the edge part of the slide opening 303. Thus, the foregoing slidable range can also be controlled by adjusting the position of the edge part of the slide opening 303 in substitute for disposing the first slide restricting part 61 and the second slide restricting part 62. For example, the adjustment may be made such that the sheet blade holder 50 comes in contact with the edge part of the front end side of the slide opening 303 at the timing that the sensor electrode 22 just reaches the target insertion depth.

Next, the user uses the control unit 200 to monitor the blood glucose level contained in the patient's bodily fluid (step S104). When the monitoring start button of the operation button 205 of the control unit 200 is pressed, the controller 203 computes the glucose concentration based on the sensor signal of the sensor 2 at predetermined intervals, and thereby monitors the blood glucose level. When the monitoring period elapses, information to the effect that the monitoring period has ended is displayed on the monitor of the control unit 200.

When the monitoring of the blood glucose level is finished, the user grips the sensor knob 51B of the sensor holder 51 and slides in the second direction along the longitudinal direction of the slide opening 303 (step S105: sensor removing step). As shown in FIG. 8B, a reduced diameter part 52A in which the diameter is gradually reduced toward the front end is formed at the apex of the locking pin. Accordingly, when the user attempts to slide the sensor knob 51B, the locked state of the locking pin 52 relative to the locking hole 30 is released based on the effect of the geometric shape of the reduced diameter part 52A. As a result, the sensor 2 is removed from the under the skin in coordination with the slide operation of the sensor knob 51B, and is returned via the lower surface opening 304 into the housing 3 (refer to FIG. 3). Note that the shape and size of the reduced diameter part 52A of the locking pin 52 are adjusted so that the locking pin 52 will not be removed from the locking hole 30 when the sheet blade knob 50B is caused to slide in the second direction, even though the locking pin 52 can be easily removed from the locking hole 30 if the user grips the sensor knob 51B and attempts to slide it in the second direction.

As described above, with the sensor insertion and removing device 1 according to this embodiment, the sheet blade holder 50 causes the puncture sheet blade 4 to slide along the guide groove 305 and, in accordance with the sliding direction thereof, selectively performs the puncture by the puncture sheet blade 4 from the lower surface opening 304 and the removing of the puncture sheet blade 4. In addition, by causing the puncture sheet blade 4 to slide along the guide groove 305 integrally with the sensor 2 upon the puncture by the puncture sheet blade 4, the sensor electrode 22 of the sensor 2 is inserted under the skin. Meanwhile, by causing the puncture sheet blade 4 to slide along the guide groove 305 in a state of being separated from the sensor 2, the puncture sheet blade 4 is removed from under the skin into the housing 3. In addition, the sensor holder 51 pulls out the sensor 2 in a state where the sensor electrode 22 is inserted under the skin and returns it via the lower surface opening 304 into the housing 3.

According to the sensor insertion and removing device 1 configured as described above, since the mechanism for inserting the sensor 2 under the skin to a predetermined depth and the entire mechanism for removing the sensor 2 from under the skin after the monitoring is finished can be integrally consolidated within the housing 2, it is possible to improve the user's convenience. In particular, after the insertion of the sensor 2 under the skin is complete, the replacement of instrumentation prior to starting the monitoring of the target substance is no longer necessary, it is easy to use and it is also possible to reduce the probability of human errors by the handler.

Moreover, since the insertion of the puncture sheet blade 4 and the sensor 2 under the skin from the housing 3 and the removing thereof from under the skin into the housing 3 are performed only via the lower surface opening 304 formed on the surface (under surface 3A) where the housing 3 is affixed to the skin, the puncture sheet blade 4 and the sensor 2 will not come in contact with the user. Thus, when the puncture sheet blade 4 is to be removed from under the skin into the housing 3 after inserting the sensor 2 under the skin or when removing the sensor 2 from under the skin into the housing 3 after the monitoring of the blood glucose level is finished, there is no fear of a third party such as a physician coming in contact with the patient's bodily fluid and getting infected. Accordingly, there is no need to take separate measures for preventing this kind of infection, and it is possible to improve the user's convenience and safety. Moreover, since the puncture sheet blade 4 is not exposed to the outside, the user will not become injured or feel any kind of psychological discomfort.

Embodiment 2

Figure 10:
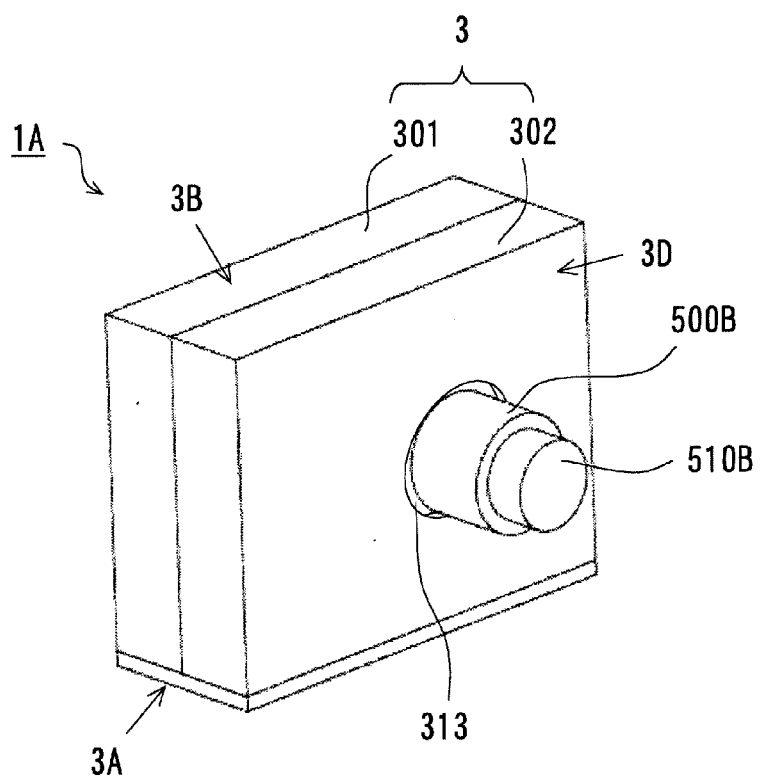
FIG. 10 is an external perspective view of the sensor insertion and removing device according to Embodiment 2.
Figure 11:
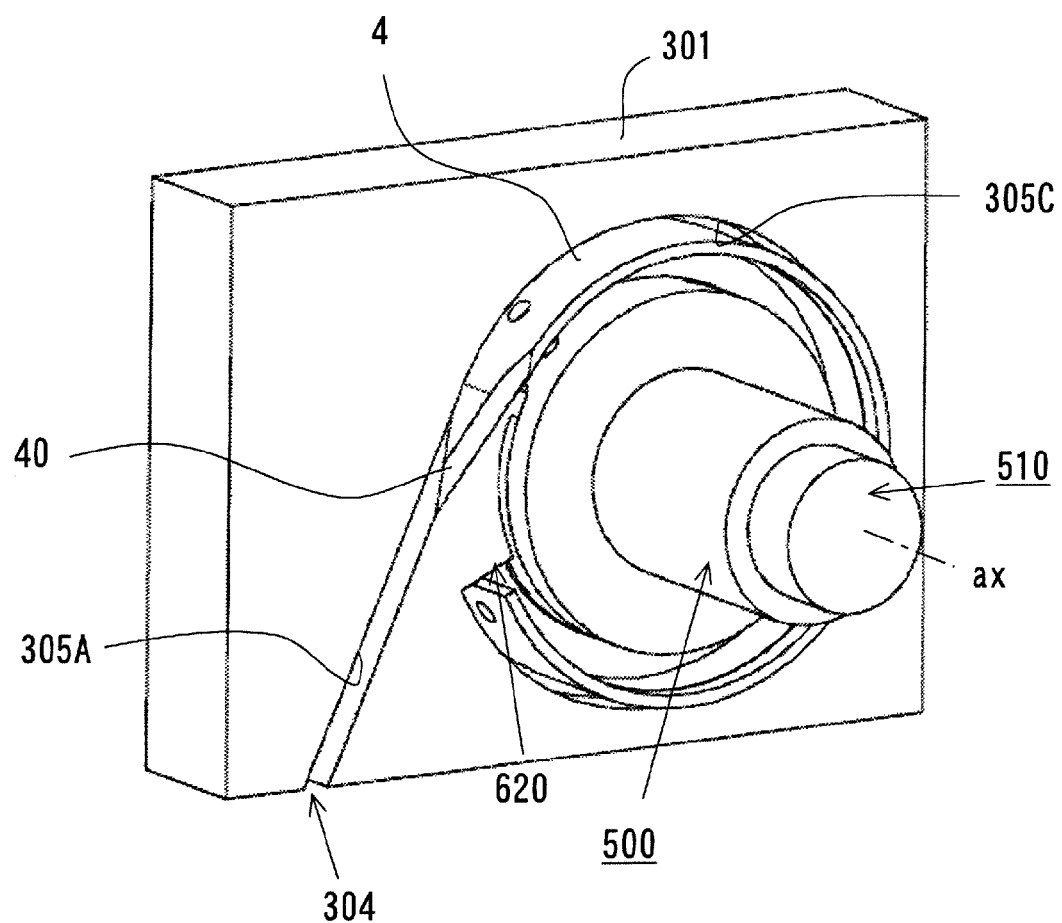
FIG. 11 is an explanatory diagram explaining the internal structure of the housing of the sensor insertion and removing device according to Embodiment 2.

The second embodiment of the sensor insertion and removing device is now explained. In the first embodiment, a so-called slide mechanism of causing the sensor knob 51B and the sheet blade knob 50B to engage in a slide operation was adopted, but in this embodiment a wind-up mechanism is used. FIG. 10 is an outer perspective view of the sensor insertion and removing device 1A according to the second embodiment. FIG. 11 is a diagram explaining the internal structure of the housing 3, and, for the sake of convenience, the illustration on the second case 302 side is omitted. With the sensor insertion and removing device 1A of this embodiment, the same members as the first embodiment are given the same reference numeral, and the detailed explanation thereof is omitted.

The guide groove 305 formed inside the housing 3 is configured from a puncture angle defining guide groove 305A, and a wind-up guide groove 305C (arc-shaped guide part) formed in an arc shape around the central axis ax. Moreover, a sheet blade holder 500 (puncture blade operating part) and a sensor holder 510 (sensor operating part) are axially supported in the housing 3, and they are respectively provided rotatably around the central axis ax.

Figure 12:
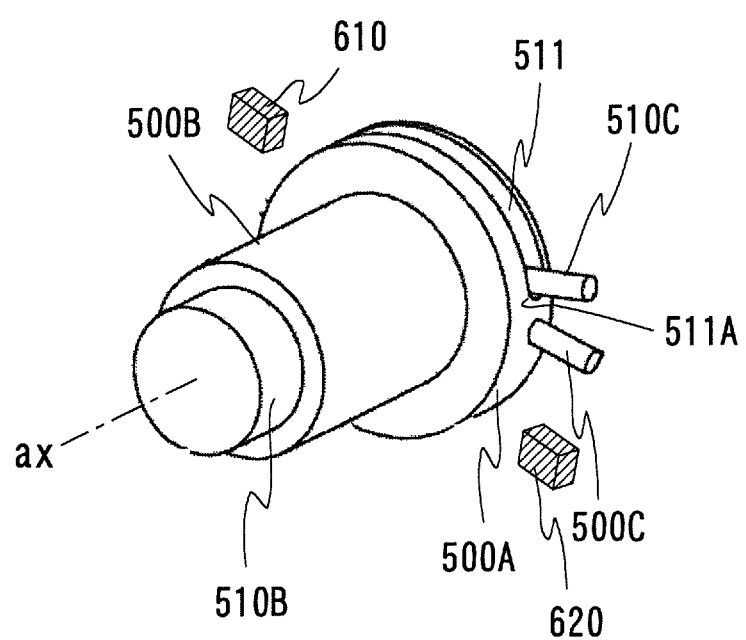
FIG. 12 is a first explanatory diagram explaining the structure of the sheet blade holder and the sensor holder of the sensor insertion and removing device according to Embodiment 2.
Figure 13:
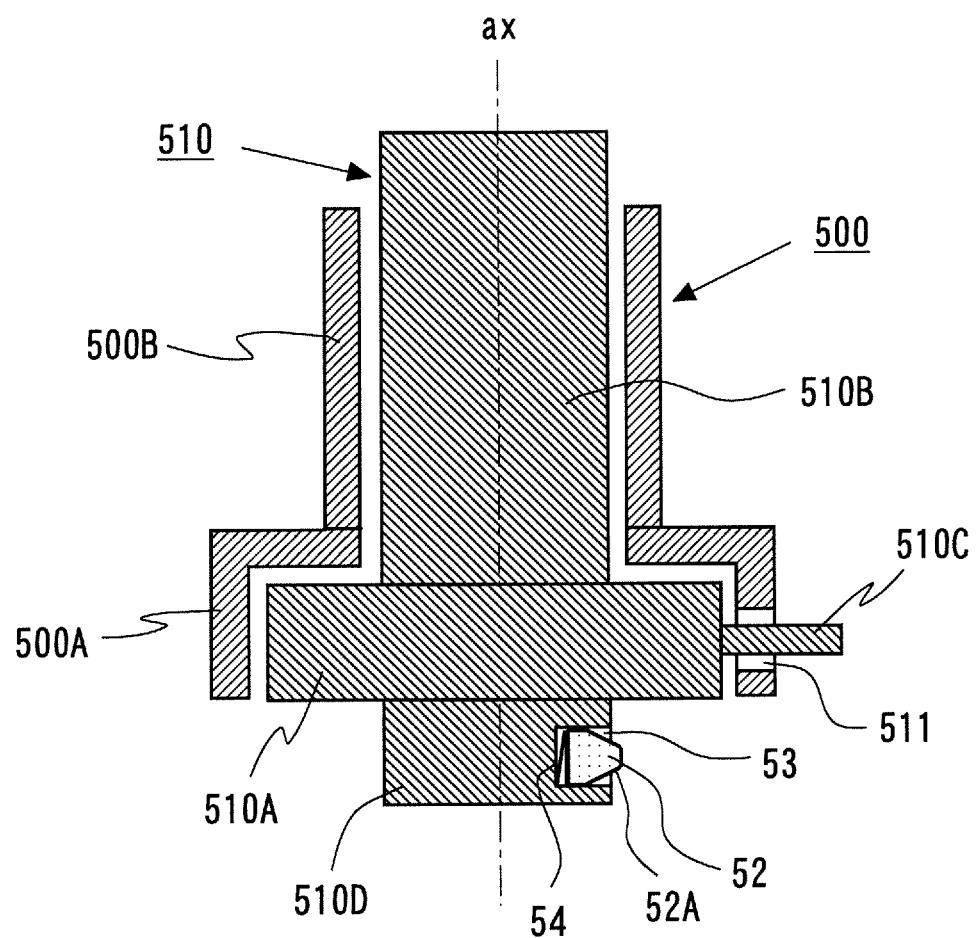
FIG. 13 is a second explanatory diagram explaining the structure of the sheet blade holder and the sensor holder of the sensor insertion and removing device according to Embodiment 2.

FIG. 12 and FIG. 13 are diagrams explaining the structure of the sheet blade holder 500 and the sensor holder 510. FIG. 12 is an outer perspective view, and FIG. 13 is a diagram showing the cross section structure. Note that, in FIG. 12 and FIG. 13, the illustrations of the sensor 2 and the puncture sheet blade 4 are omitted.

The sensor holder 510 includes a base part 510A, a sensor knob 510B, a sensor joint part 510C, and a locking pin holding part 510D. The base part 510A, the sensor knob 510B, and the locking pin holding part 510D are respectively cylindrical members in which their axis coincides with the central axis ax. The sensor knob 510B and the locking pin holding part 510D are formed to have a diameter that is one level narrower than the base part 510A. The sensor joint part 510C is jointed to the base end part 21B (second basic portion) of the sensor 2. A housing concave part 53 is formed on the locking pin holding part 510D, and the spring member 54 and the locking pin 52 are housed therein.

Moreover, the sheet blade holder 500 is formed in a tubular shape so as to cover the outer periphery of the base part 510A and the sensor knob 510B of the sensor holder 510. The sheet blade holder 500 includes a cylindrical base tube part 500A which covers the outer periphery of the base part 510A, a sheet blade knob 500B, and a sheet blade joint part 500C. The sheet blade knob 500B is a cylindrical member which covers the outer periphery of the sensor knob 510B in which its diameter is reduced to be smaller than the base tube part 500A. The sheet blade joint part 500C is a member that is jointed to the back end part 41 (first basic portion) of the puncture sheet blade 4 by being integrally formed with the base tube part 500A.

The sensor knob 510B and the sheet blade knob 500B positioned around the outer periphery thereof are disposed concentrically, and the front end side of the sensor knob 510B is protruding from the front end side of the sheet blade knob 500B. Moreover, the base tube part 500A is formed with an elongated hole 511 for allowing the insertion of the sensor joint part 510C, which is provided in a protruding manner in the radial direction from the base part 510A disposed on the inside thereof, along the circumferential direction of the base tube part 500A. The elongated hole 511 is formed, for example, across a range of approximately ¾ of a circle in the circumferential direction of the base tube part 500A, but this range can be changed as needed. Moreover, the sheet blade joint part 500C is provided in a protruding manner in the radial direction from the vicinity of the edge part of the elongated hole 511 in the base tube part 500A.

As shown in FIG. 10, a circular operation opening 313 is formed on the side surface 3D of the housing 3. With the sensor knob 510B and the sheet blade knob 500B, their respective front end sides are exposed to the outside of the housing 3 as a result of being inserted through the operation opening 313. However, the shape of the operation opening 313 is not limited to the foregoing example. Moreover, as described in detail later, when the user is to operate the sensor insertion and removing device 1A, the operation opening 313 is provided to a surface that is other than the under surface 3A to be fixed to the skin and to a surface through which the central axis ax of the wind-up guide groove 305C penetrates in light of the configuration where the sheet blade knob 500B and the sensor knob 510B protruding outside the housing 3 are operated by being rotated via the operation opening 313.

The sensor 2 and the puncture sheet blade 4 in the sensor insertion and removing device 1A are the same as those explained in the first embodiment. In the initial state, the sensor 2 is received slidably in the long groove 43 of the puncture sheet blade 4. Moreover, the puncture sheet blade 4 is glidably (slidably) supported, from its front end side, by the guide groove 305 configured from the puncture angle defining guide groove 305A and the wind-up guide groove 305C. The puncture sheet blade 4 can be caused to slide along the guide groove 305 (puncture angle defining guide groove 305A and wind-up guide groove 305C) by rotating the sheet blade knob 500B of the sheet blade holder 500, and the puncture and removing of the puncture sheet blade 4 through the lower surface opening 304 are selectively performed according to the sliding direction thereof. In this embodiment, when the sheet blade knob 500B is rotated counterclockwise (first direction), the wind-up amount of the puncture sheet blade 4 to the wind-up guide groove 305C is reduced, and when the sheet blade knob 500B is rotated clockwise, the wind-up amount of the puncture sheet blade 4 is increased.

The operation of the sensor insertion and removing device 1 is now explained. Foremost, the user disposes the housing 3 at a predetermined position on the skin (setup step). In this state, the appearance of the sensor insertion and removing device 1A is in the initial state shown in FIG. 10. Next, the user rotates the sheet blade knob 500B counterclockwise (first direction) (sensor insertion step). Then, the sensor joint part 510C that is contact with the edge part 511A of the elongated hole 511 also rotated counterclockwise in conjunction therewith, and the sensor 2 received in the long groove 43 of the puncture sheet blade 4 is also operated passively. Consequently, the puncture sheet blade 4 slides toward the front end side of the guide groove 305 integrally with the sensor 2. In addition, the puncture sheet blade 4 punctures the skin as a result of the blade edge part 40 being delivered from the lower surface opening 304, and the sensor 2 that is received in the puncture sheet blade 4 is also inserted under the skin.

The first rotation restricting part 610 and the second rotation restricting part 620 shown in FIGS. 11 and 12 are members for defining the rotatable range of the sensor knob 510B and the sheet blade knob 500B, and are provided integrally with the housing 3. With the first rotation restricting part 610, when the user grips the sheet blade knob 500B and rotates it counterclockwise (first direction), the sensor joint part 510C of the sensor holder 510 comes in contact with the first rotation restricting part 610. Consequently, the further rotating operation of the sensor knob 510B in the first direction is restricted. As a result, the edge part 511A of the elongated hole 511 interferes with the sensor joint part 510C, and the counterclockwise rotating operation of the sheet blade knob 500B is restricted. In other words, the rotating operation of the sheet blade holder 500 is indirectly restricted by the first rotation restricting part 610 via the sensor holder 510. As a result, the puncture sheet blade 4 can no longer be delivered from the housing 3, and the blade edge part 40 will no longer slide deeper into the skin.

The first rotation restricting part 610 is provided at a position where the sensor joint part 510C comes in contact with the first rotation restricting part 610 at the time that the sensor electrode 22 reaches the target insertion depth. The user is thereby able to reliably cause the sensor electrode 22 to reach the target insertion depth by rotating the sheet blade knob 500B counterclockwise until it is restricted by the first rotation restricting part 610. Then, after the sensor electrode 22 reaches the target insertion depth, the sensor electrode 22 will not be inserted any deeper. As a result, the sensor electrode 22 can be inserted to the target insertion depth in just proportion.

As with the sensor insertion and removing device 1 according to the first embodiment, a locking hole 30 for locking the locking pin 52 is formed on the inner wall surface 3C of the housing 3 in the sensor insertion and removing device 1A. Upon referring to FIG. 8, in this embodiment, reference numeral 51A in the diagram is substituted by reference numeral 510D (locking pin holding part). In the housing 3, the inner wall surface 3C positioned around the locking pin holding part 510D is formed in a tube shape of covering the cylindrical side surface of the locking pin holding part 510D. When the sheet blade knob 500B is rotated counterclockwise, the locking hold 3D is provided at a position where the locking pin 52 becomes fitted with the locking hole 30 at the time that the sensor knob 510B just comes in contact with the first rotation restricting part 610.

Figure 14A:
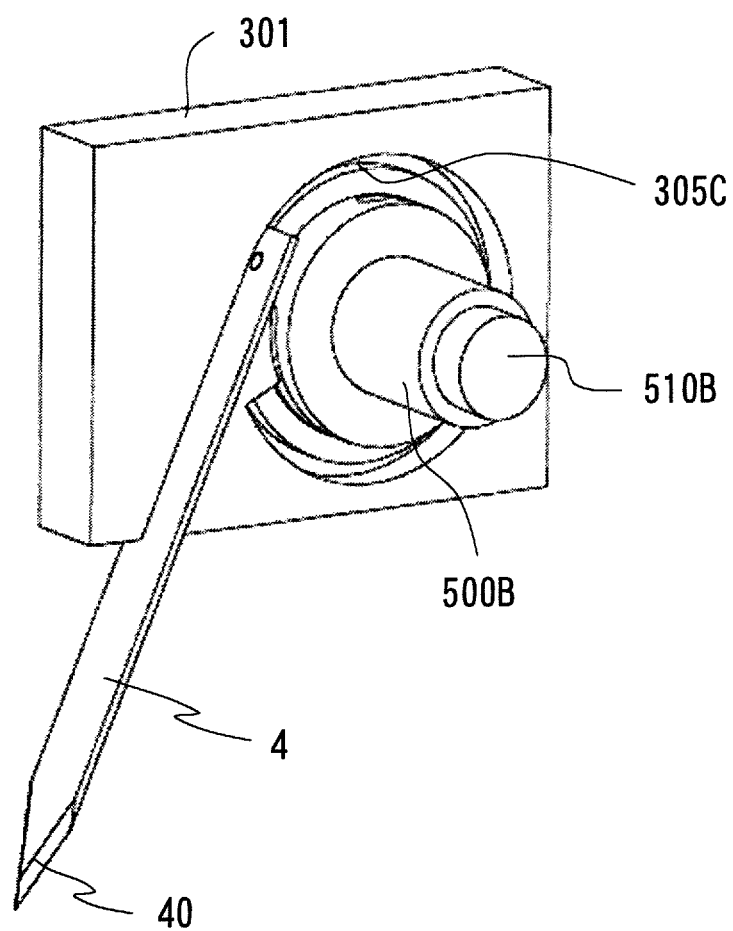
FIG. 14A is a diagram showing a state where the puncture of the puncture sheet blade is complete in the sensor insertion and removing device according to Embodiment 2.
Figure 14B:
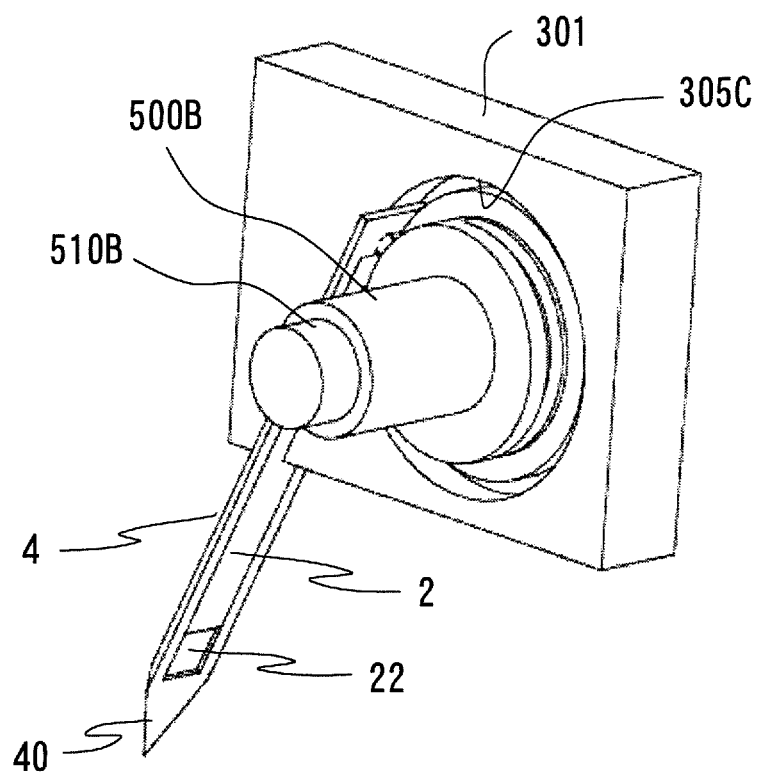
FIG. 14B is a diagram showing a state where the puncture of the puncture sheet blade is complete in the sensor insertion and removing device according to Embodiment 2.

According to the above, the locking pin holding part 510D rotates while causing the apex of the locking pin 52 to come in slidable contact with the inner wall surface 3C until the sensor knob 510B comes in contact with the first rotation restricting part 610. Then, the locking pin 52 is fitted with the locking hole 30 at the time that the sensor knob 510B comes in contact with the first rotation restricting part 610. FIGS. 14A and 14B show a state where the puncture by the puncture sheet blade 4 is complete. In this state, the sensor electrode 22 of the sensor 2 is disposed at a predetermined target insertion depth.

Next, the user grips only the sheet blade knob 500B of the sheet blade holder 500, and rotates the sheet blade knob 500B clockwise (puncture blade removing step). As a result, the base tube part 500A that is integral with the sheet blade knob 500B also rotates clockwise. Contrarily, since the edge part 511A of the elongated hole 511 breaks away from the sensor joint part 510C, the foregoing components will not interfere with each other. Here, the locking pin 52 provided to the sensor holder 510 side is locked by the locking hole 30. Thus, when the sheet blade knob 500B is rotated clockwise, the long groove 43 of the puncture sheet blade 4 causes the sensor 2 to slide, and the fitted state of the sensor 2 in the long groove 43 is released. Consequently, the guide groove 305 will slide in a state where the puncture sheet blade 4 is separated from the sensor 2, and only the puncture sheet blade 4 is removed from under the skin in a state where the sensor 2 is implanted under the skin.

Figure 15:
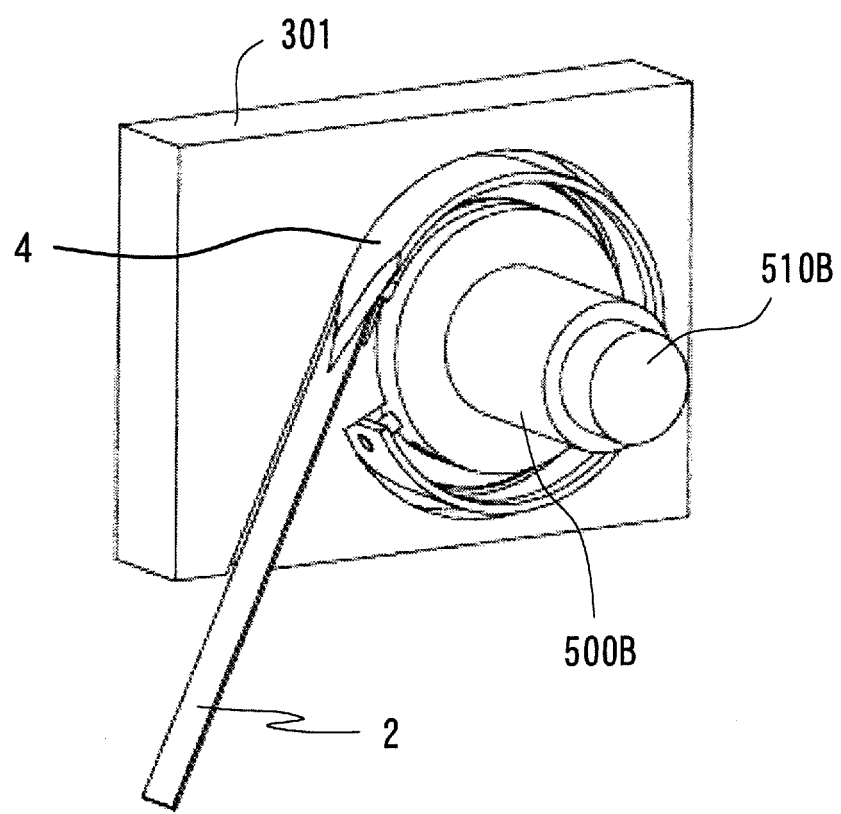
FIG. 15 is a diagram showing a state where the removing of the puncture sheet blade is complete in the sensor insertion and removing device according to Embodiment 2.

When the sheet blade knob 500B is rotated in the clockwise direction, the sheet blade joint part 500C of the sheet blade holder 500 will ultimately come in contact with the second rotation restricting part 620. Then, at the time the sheet blade joint part 500C comes in contact with the second rotation restricting part 620, the moving operation of the sensor knob 510B in the clockwise direction is restricted (prohibited). As a result, the sliding of the puncture sheet blade 4 in the guide groove 305 is stopped. The position of disposing the second rotation restricting part 620 is adjusted so that the blade edge part 40 of the puncture sheet blade 4 is completely housed in the housing 3 at the time that the second rotation restricting part 620 comes in contact with the sheet blade joint part 500C of the sheet blade holder 500. FIG. 15 is a diagram showing a state where the removing of the puncture sheet blade in this embodiment is complete. In other words, FIG. 15 shows a state where the blade edge part 40 is returned via the lower surface opening 304 into the housing 3 and a state where only the sensor 2 is implanted under the skin. Note that, in FIG. 14 and FIG. 15 as well, the illustration of the second case 302 side is omitted for the sake of convenience.

Next, the user uses the control unit 200 to monitor the blood glucose level contained in the patient's bodily fluid. When the monitoring is finished, the user grips the sensor knob 510B of the sensor holder 510 and rotates it clockwise (sensor removing step). As with the first embodiment, a reduced diameter part 52A is formed at the apex of the locking pin 52. Thus, as a result of a clockwise rotating force working on the sensor knob 510B, the locked state of the locking hole 30 and the locking pin 52 is released. Consequently, the sensor 2 is pulled out from under the skin in coordination with the rotating operation of the sensor knob 510B, and returned via the lower surface opening 304 into the housing 3 (refer to FIG. 11).

As described above, with the sensor insertion and removing device 1A according to this embodiment, in addition to yielding the same operation and effect as the first embodiment, the device can be further downsized as a result of adopting a so-called wind-up mechanism.

Embodiment 3

Figure 16:
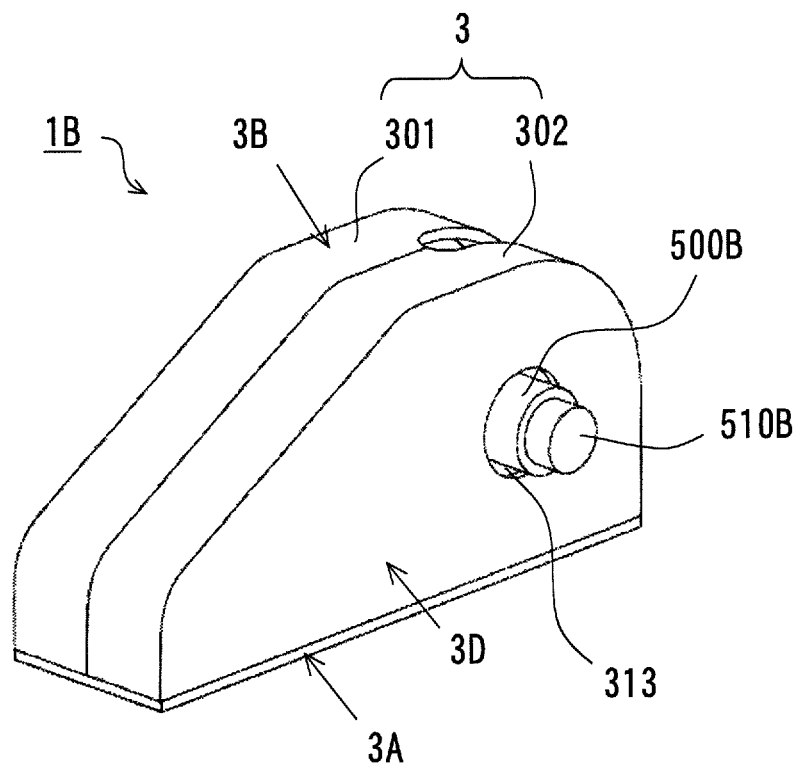
FIG. 16 is a first external perspective view of the sensor insertion and removing device according to Embodiment 3.
Figure 17:
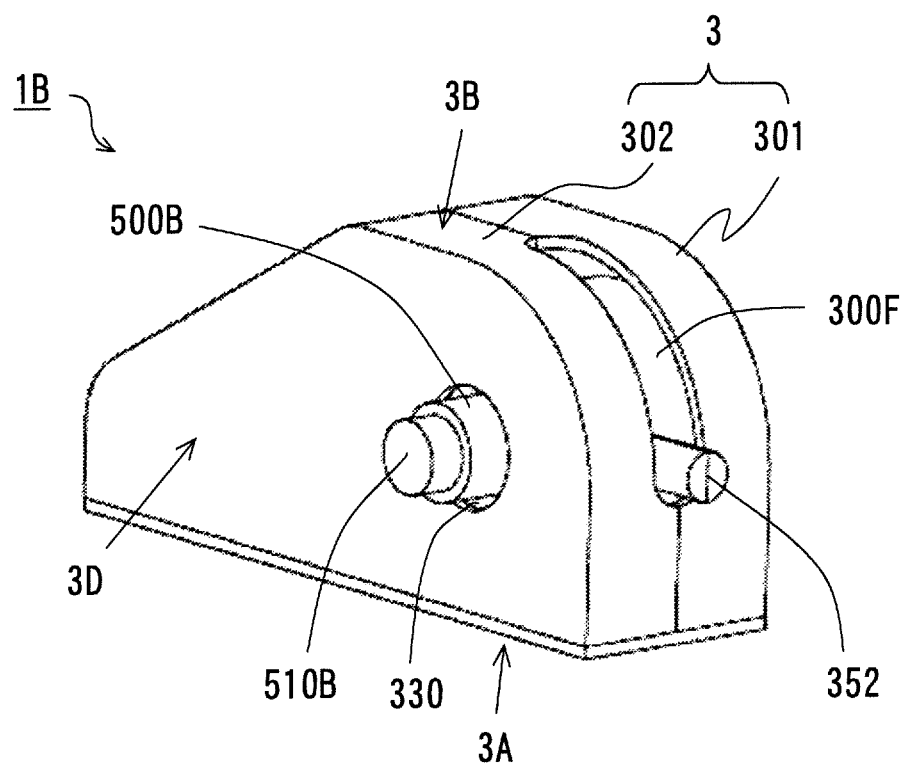
FIG. 17 is a second external perspective view of the sensor insertion and removing device according to Embodiment 3.
Figure 18:
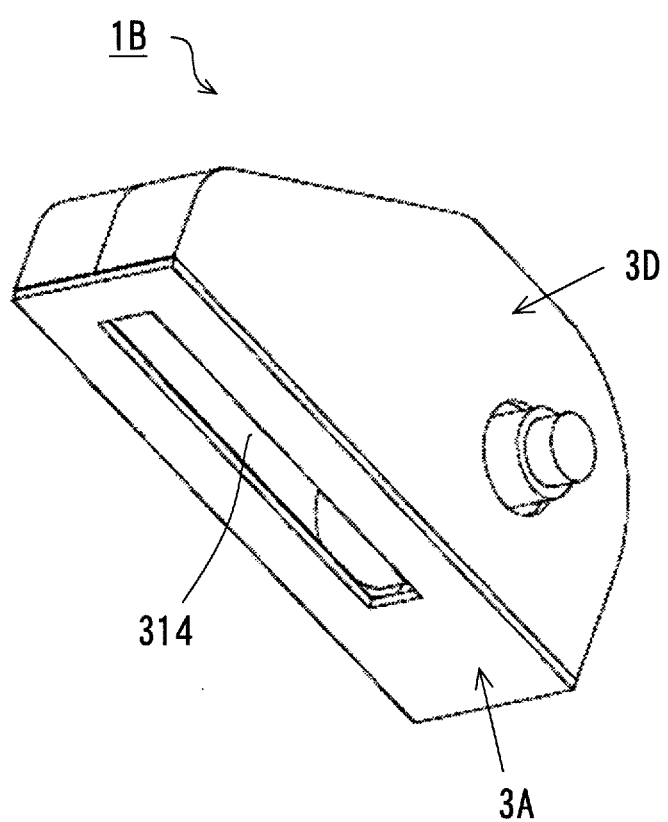
FIG. 18 is a third external perspective view of the sensor insertion and removing device according to Embodiment 3.

The third embodiment is now explained. FIG. 16 to FIG. 18 are outer perspective views of the sensor insertion and removing device 1B according to the third embodiment. In the sensor insertion and removing device 1B according to this embodiment, the same member as those of the first and second embodiments are given the same reference numeral, and the detailed explanation thereof is omitted. The sensor insertion and removing device 1B of this embodiment is characterized in that the puncture angle of the puncture sheet blade 4 relative to the skin can be changed, and the other points are basically the same as the sensor insertion and removing device 1A according to the second embodiment.

A lower surface opening 314 is formed on the under surface 3A of the housing 3. The lower surface opening 314 relatively larger than the lower surface opening 304 of the first and second embodiments, but possesses the same function as the lower surface opening 304 from the perspective that it is an opening for performing the insertion and the removing of the sensor 2 and the puncture sheet blade 4 to and from under the skin. Note that, in this embodiment, the reason why the area of the lower surface opening 314 was increased is in order to avoid the puncture sheet blade 4 interfering with the lower surface opening 314 even when the puncture angle is changed.

Figure 19:
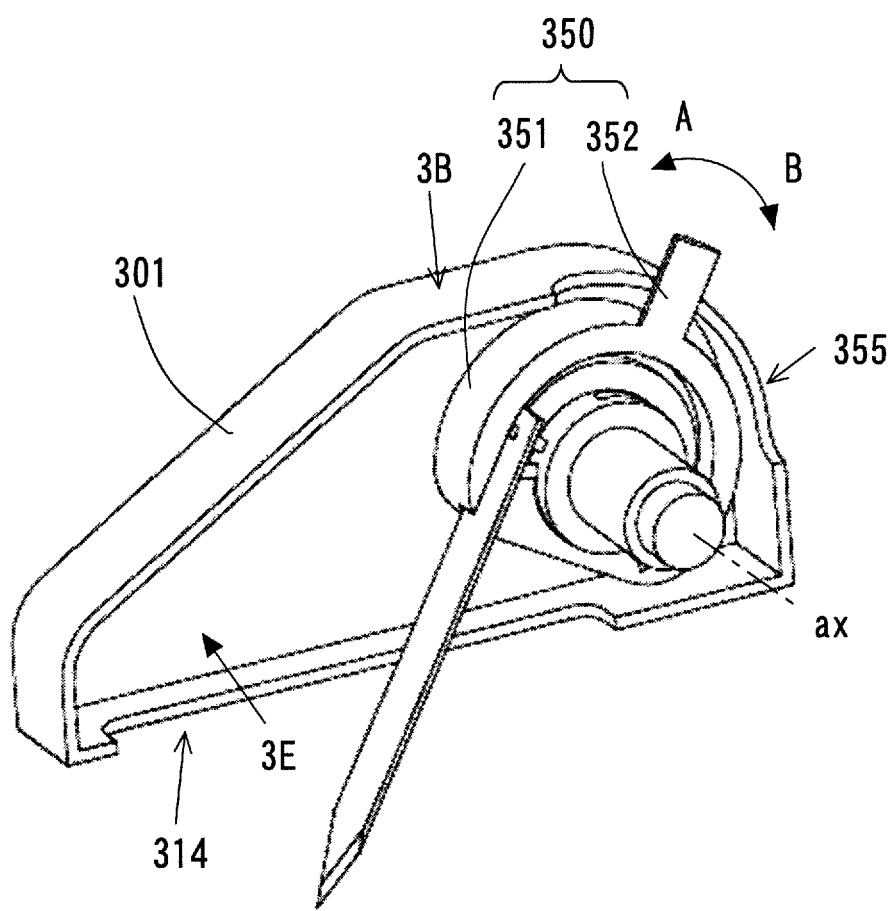
FIG. 19 is a first explanatory diagram of the internal structure of the housing of the sensor insertion and removing device according to Embodiment 3.
Figure 20:
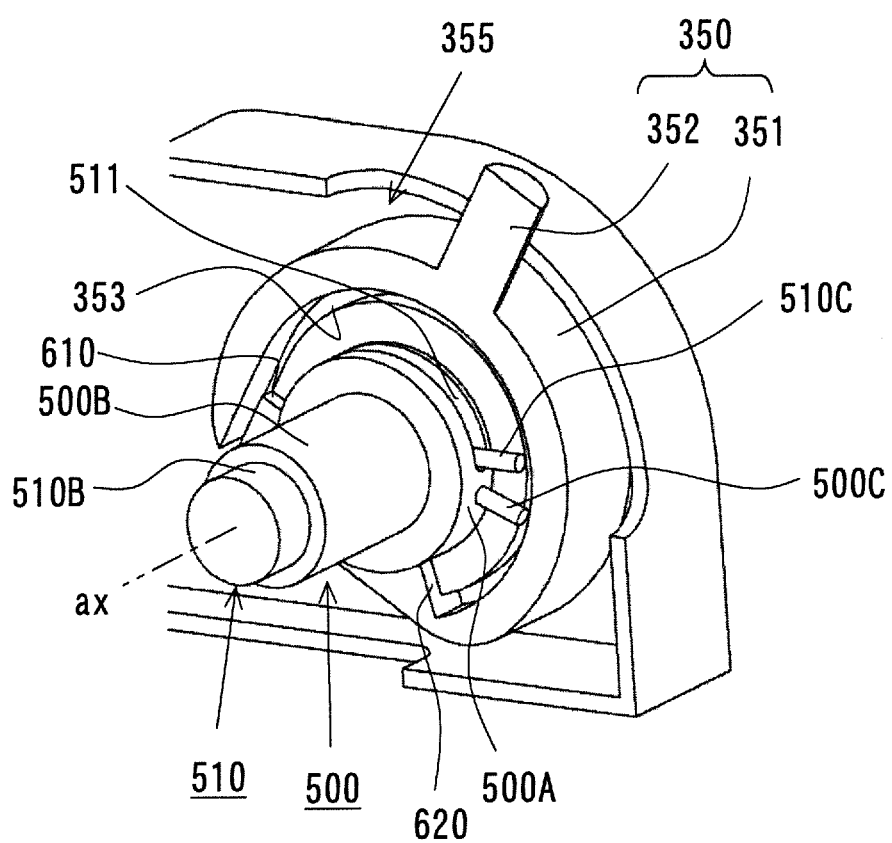
FIG. 20 is a second explanatory diagram of the internal structure of the housing of the sensor insertion and removing device according to Embodiment 3.

FIG. 19 and FIG. 20 are diagram explaining the internal structure of the housing 3, and, for the sake of convenience, the illustration of the second case 302 side is omitted. Inside the housing 3, the guiderail holder 350 is swingably and axially supported by the side surface 3D of the housing 3 and the side surface 3E which is positioned opposite thereto. The swing axis of the guiderail holder 350 is coaxial with the "central axis ax" as the rotation axis of the sheet blade holder 500 and the sensor holder 510. The guiderail holder 350 includes a guide body part 351 that is formed in a substantially U-shape, and a rod-like operation lever 352 that is formed integrally with the guide body part 351. A guiderail 353 (arc-shaped guide part) which slidably (glidably) supports the puncture sheet blade 4 is formed in an arc shape around the central axis ax on the inner peripheral side of the guide body part 351.

The boundary part of the side surface which is sandwiched by the side surface 3D and the side surface 3E, and the upper surface 3B is formed in a curved surface shape so that both surfaces become connected gradually, and an elongated opening (hereinafter referred to as the "swing operation opening") 355 is formed at the boundary part. The operation lever 352 is extending from the guide body part 351 toward a direction that is orthogonal to the central axis ax, and faces the outside of the housing 3 as a result of its front end side being inserted through the swing operation opening 355. Moreover, the sheet blade holder 500 and the sensor holder 510 are the same as those in the second embodiment. Furthermore, the basic operation of inserting and removing the sensor 2 to and from under the skin is as explained in the second embodiment, and the explanation thereof is omitted.

The guiderail holder 350 is swingable within a predetermined range. The swing angle of the guiderail holder 350 relative to the central axis ax can be changed by the user operating the operation lever 352 in the direction of arrow A or the direction of arrow B in FIG. 19. The stop position of the guiderail holder 350 can be set in stages in advance such as, for example, swing stop position A, B, C, . . . . In addition, the housing 3 is provided with a lock mechanism (not shown) which automatically locks the guiderail holder 350; that is, stops the guiderail holder 350 at that position when the swing angle of the guiderail holder 350 becomes an angle corresponding to any one of the set swing stop positions A, B, C, . . . . In addition, this lock mechanism also has the function of releasing the foregoing locked state according to operations such as the pressing of the unlock button.

Figure 21A:
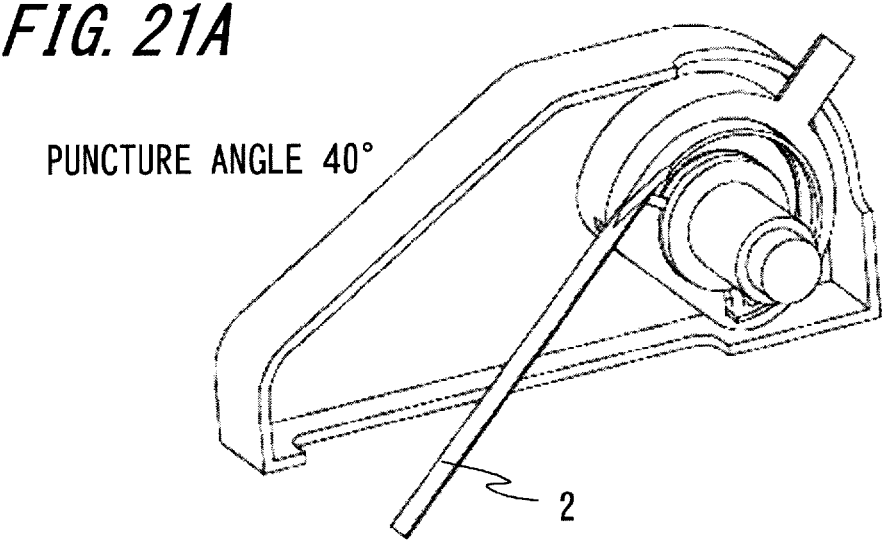
FIG. 21A is a diagram showing a state where the sensor is inserted under the skin upon adjusting the puncture angle to 40° in the sensor insertion and removing device according to Embodiment 3.
Figure 21B:
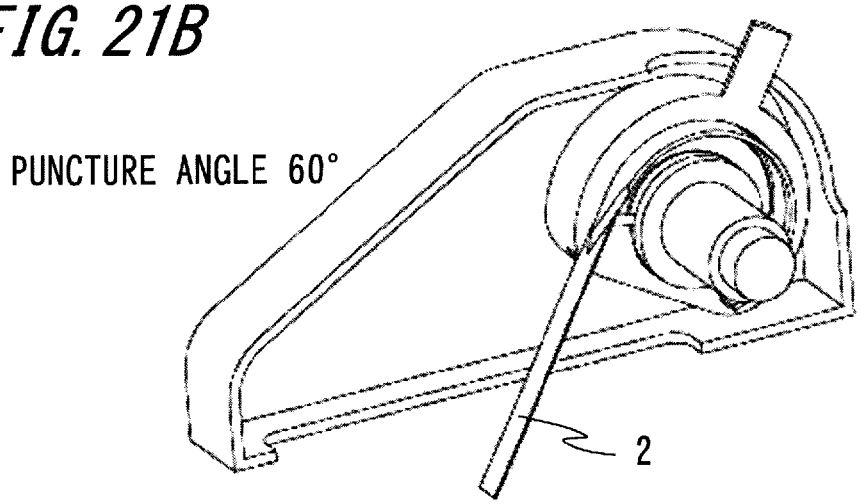
FIG. 21B is a diagram showing a state where the sensor is inserted under the skin upon adjusting the puncture angle to 60° in the sensor insertion and removing device according to Embodiment 3.
Figure 21C:
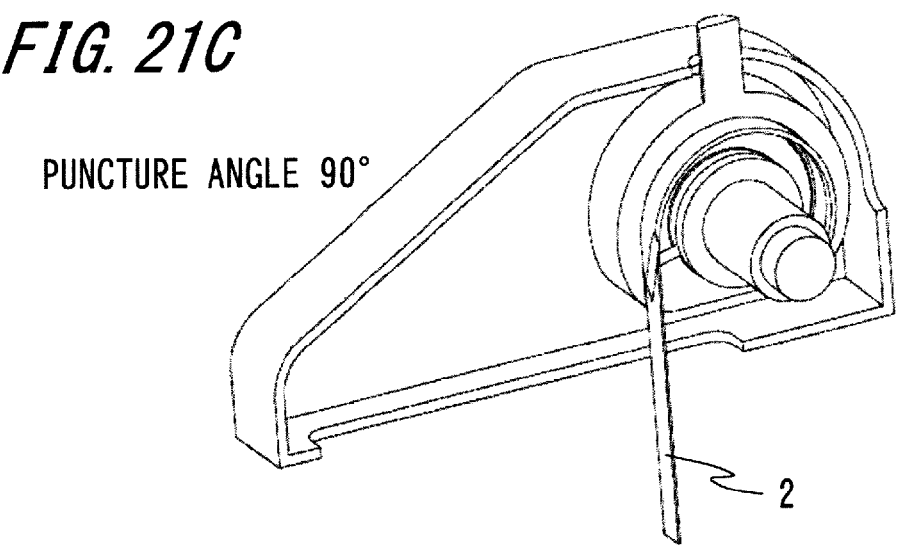
FIG. 21C is a diagram showing a state where the sensor is inserted under the skin upon adjusting the puncture angle to 90° in the sensor insertion and removing device according to Embodiment 3.

In this embodiment, the guiderail holder 350 corresponds to the puncture angle adjustment unit. By changing the swing stop position of the guiderail holder 350, the puncture angle of the puncture sheet blade 4 to the skin can be changed. Note that the term "puncture angle" as used herein is defined as an angle that is formed by the lower surface of the housing that is affixed to the skin and the puncture sheet blade 4 that punctures the skin. FIG. 21 shows the respective states of adjusting the puncture angle to 40°, 60° and 90° and inserting the sensor 2 under the skin. Note that the setting of the puncture angles shown in the respective diagrams is merely an exemplification, and the size of the angle, number of settings and the like may be changed as needed. Moreover, although the puncture angle of the puncture sheet blade 4 is adjusted in stages by setting a plurality of swing stop positions of the guiderail holder 350 in the foregoing example, it can also be adjusted in a stepless manner.

Meanwhile, as the puncture angle of the puncture sheet blade 4 is smaller, the insertion of the puncture sheet blade 4 and the sensor 2 under the skin becomes more gentle. Thus, when using the same type of sensor 2, the insertion depth of the sensor electrode 22 can be adjusted by adjusting the puncture angle. Meanwhile, upon monitoring the blood glucose level, the deeper the insertion depth of the sensor 2, it can be said that the monitoring result becomes more reliable since it is possible to facilitate the contact of glucose to the sensor electrode. Nevertheless, to deepen the insertion depth of the sensor 2 means that the puncture sheet blade 4 needs to puncture the skin more deeply, and there are demands for making the insertion depth of the sensor 2 to be as shallow as possible from the perspective of alleviating the pain during the puncture. In response, since the sensor insertion and removing device 1B in this embodiment can adjust the puncture angle of the puncture sheet blade 4, it is possible to achieve a balance between the reliability of the monitoring result and the alleviation of pain during the puncture.

Moreover, the level of pain that is felt by the patient during the puncture will vary among different individuals even if the puncture depth is the same. For example, upon comparing patients with sparse subcutaneous fat and patients with abundant subcutaneous fact, it is considered that the latter patients will feel less pain during the puncture. Moreover, there are patients who are sensitive to pain during the puncture and patients who are not so sensitive. Thus, by adjusting the puncture angle of the puncture sheet blade 4 according to the individual differences of the patients by using the sensor insertion and removing device 1B of this embodiment, it is possible to perform the insertion operation of sensors, which was conventionally uniform, by giving consideration to the individual differences of the patients.

Moreover, there are cases where a plurality of types of sensors in which the area of the sensor electrode 22 is different by being large or small are prepared as a lineup. When using a sensor with a large sensor electrode 22, the glucose in the bodily fluid can come into contact with the sensor electrode easier in comparison to the case of using a sensor with a small sensor electrode 22. Accordingly, it is possible to reduce the puncture angle while maintaining the reliability of the monitoring result, and further alleviate the pain during the puncture. Moreover, when attempting to detect a component other than glucose such as cholesterol or lactic acid with a sensor, there are cases where the optimal insertion depth is different according to the detection target. In response, according to the sensor insertion and removing device 1B, since the insertion depth of the sensor can be adjusted by adjusting the puncture angle of the puncture sheet blade 4, it is possible to flexibly deal with changes in the target insertion depth of the sensor.

Note that the adjustment of the puncture angle of the puncture sheet blade 4 by the guiderail holder 350 (puncture angle adjustment unit) can be favorably performed prior to inserting the sensor 2 under the skin. Here, in the method of inserting and removing the sensor in this embodiment, the step (puncture angle adjustment step) of adjusting the puncture angle of the puncture sheet blade 4 by changing the swing stop position of the guiderail holder 350 relative to the housing 3 is performed before the step (sensor insertion step) of inserting the sensor 2.

Embodiment 4

Figure 22:
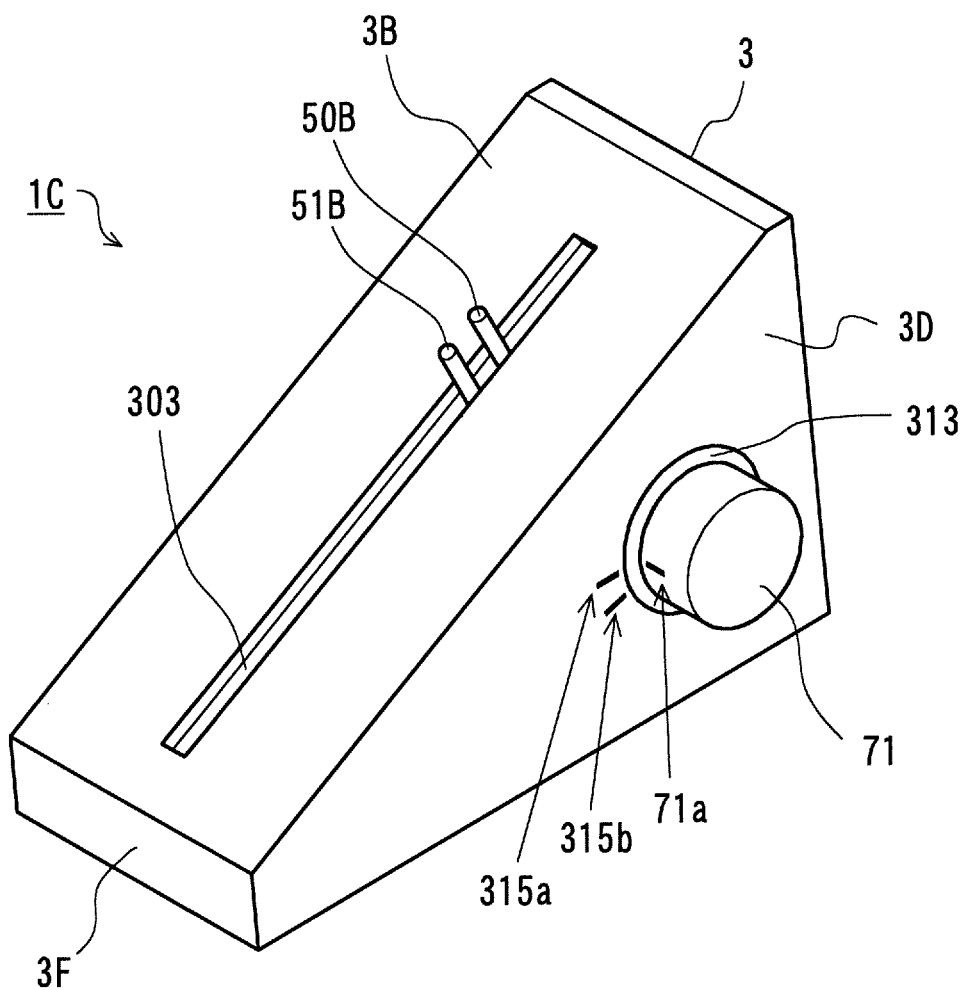
FIG. 22 is an external perspective view of the sensor insertion and removing device according to Embodiment 3.
Figure 23:
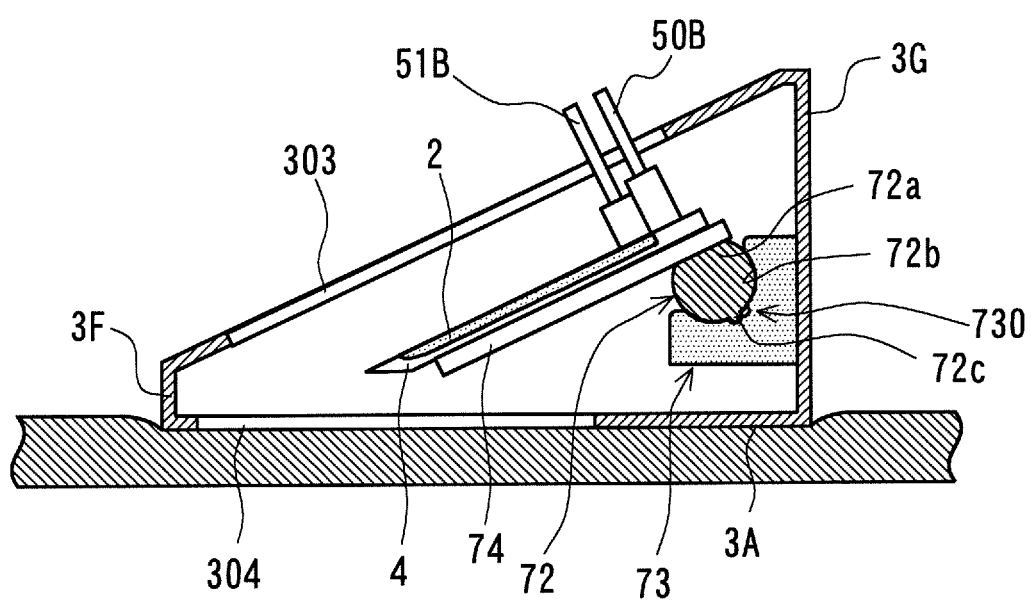
FIG. 23 is an internal structural diagram of the sensor insertion and removing device according to Embodiment 4.
Figure 24:
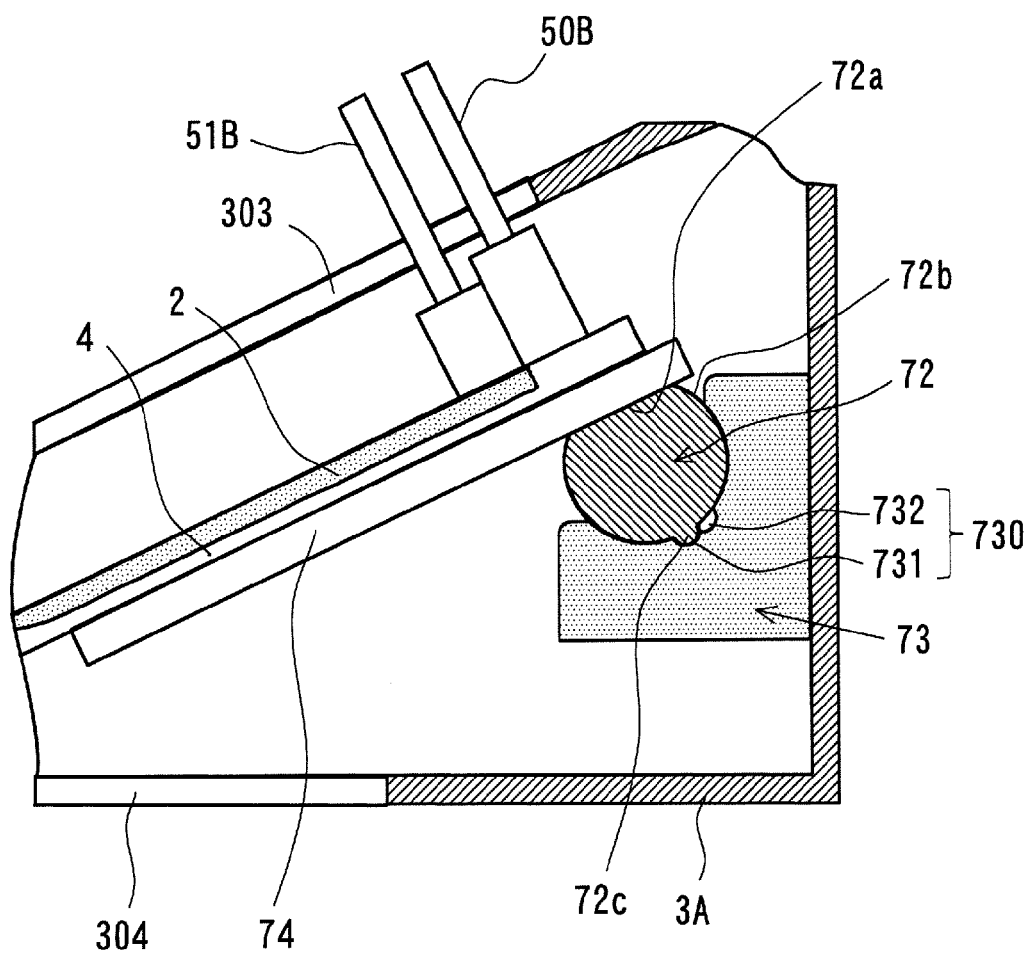
FIG. 24 is a partially enlarged view of FIG. 23.

The fourth embodiment is now explained. FIG. 22 is an external perspective view of the sensor insertion and removing device 1C according to Embodiment 4. FIG. 23 is an internal structural diagram of the sensor insertion and removing device 1C according to Embodiment 4. FIG. 23 represents the cross section of the sensor insertion and removing device 1C. Moreover, FIG. 24 is a partially enlarged view of FIG. 23. In the sensor insertion and removing device 1C according to this embodiment, members that are the same as Embodiments 1 to 3 are given the same reference numeral and the detailed explanation thereof is omitted. The sensor insertion and removing device 1C comprises a mechanism capable of changing the puncture angle of the puncture sheet blade 4 as explained in Embodiment 3. This embodiment explained a case of applying the mechanism capable of changing the puncture angle to a slide-type sensor insertion and removing device as with Embodiment 1.

The configuration of the sensor insertion and removing device 1C in this embodiment 4 will be described, mainly on the points of difference from the sensor insertion and removing device 1 according to Embodiment 1. With the sensor insertion and removing device 1C, the upper surface 3B of the housing 3 is inclined forward and downward from the rear surface 3G side toward the front surface 3F side. The housing 3 internally houses a unit configured from the sensor 2, the puncture sheet blade 4 and the like which are substantially the same as those shown in FIG. 5. A slide opening 303 is formed on the upper surface 3B as in Embodiment 1. A sheet blade knob 50B and a sensor knob 51B are inserted through the slide opening 303, and the user slides the sheet blade knob 50B and the sensor knob 51B to insert the sensor 2 and the puncture sheet blade 4 under the skin and remove the same from under the skin.

The sensor insertion and removing device 1C comprises a puncture angle adjustment mechanism capable of adjusting the puncture angle upon puncturing the skin with the puncture sheet blade 4. The puncture angle adjustment mechanism includes an angle adjustment knob 71, a shaft member (a angle adjustment shaft part) 72, a bearing member 73 and the like. The bearing member 73 is fixed to the inside of the rear surface 3G of the housing 3. The angle adjustment shaft part 72 is a shaft member taking on a shape in which a part of the peripheral surface of a columnar member is of a planar shape.

Of the peripheral surface of the angle adjustment shaft part 72, the planar shaped portion is referred to as a planar surface part 72a, and the curved surface portion is referred to as a curved surface part 72b. The curved surface part 72b of the angle adjustment shaft part 72 is provided with a protrusive convex part 72c positioned at a side that is opposite to the planar surface part 72a. The convex part 72c is formed along the axis of member direction of the angle adjustment shaft part 72.

The bearing member 73 is a member for rotatably bearing the angle adjustment shaft part 72. The bearing member 73 includes a bearing surface 73a which slidably supports the curved surface part 72b of the angle adjustment shaft part 72. A part of the bearing surface 73a is formed with a concave part 730 (first concave part 731, second concave part 732) to which is fitted the convex part 72c formed on the curved surface part 72b of the angle adjustment shaft part 72. The bearing member 73 is formed across the entire width range from the inner wall of one lateral inner surface to the other lateral inner surface in the housing 3. As shown in FIG. 23 and FIG. 24, the angle adjustment shaft part 72 is supported by the bearing member 73 in a state where its curved surface part 72b is contact with the bearing surface 73a. Moreover, the convex part 72c of the angle adjustment shaft part 72 can be fitted to either the first concave part 731 or the second concave part 732, and, in the example shown in FIG. 24, the convex part 72c is fitted to the first concave part 731.

The angle adjustment knob 71 is mounted on one end of the angle adjustment shaft part 72. The shaft center of the angle adjustment knob 71 and the shaft center of the angle adjustment shaft part 72 coincide. As shown in FIG. 22, the angle adjustment knob 71 has a columnar shape, and is exposed outside the housing 3 by being inserted through the circular operation opening 313 formed on the side surface 3D of the housing 3.

A puncture sheet blade 4 is mounted on the planar surface part 72a of the angle adjustment shaft part 72 via a guide member 74. With the guide member 74, the bottom part of the base end side is fixed to the planar surface part 72a, and the tip side is configured to take on a cantilever shape. Accordingly, the correlation of the rotating angle of the angle adjustment shaft part 72 and the inclination angle of the guide member 74 is constant. The puncture sheet blade 4 is mounted slidably in the front and rear direction along the guide member 74. Note that the guide member 74 has a guide mechanism (for example, a C-type channel member provided on either end in the width direction of the guide member 74) which only allows the sliding operation to the front and rear direction of the puncture sheet blade 4 relative to the guide member 74, and restricts the rotational operation in the vertical direction and the horizontal direction.

Figure 25:
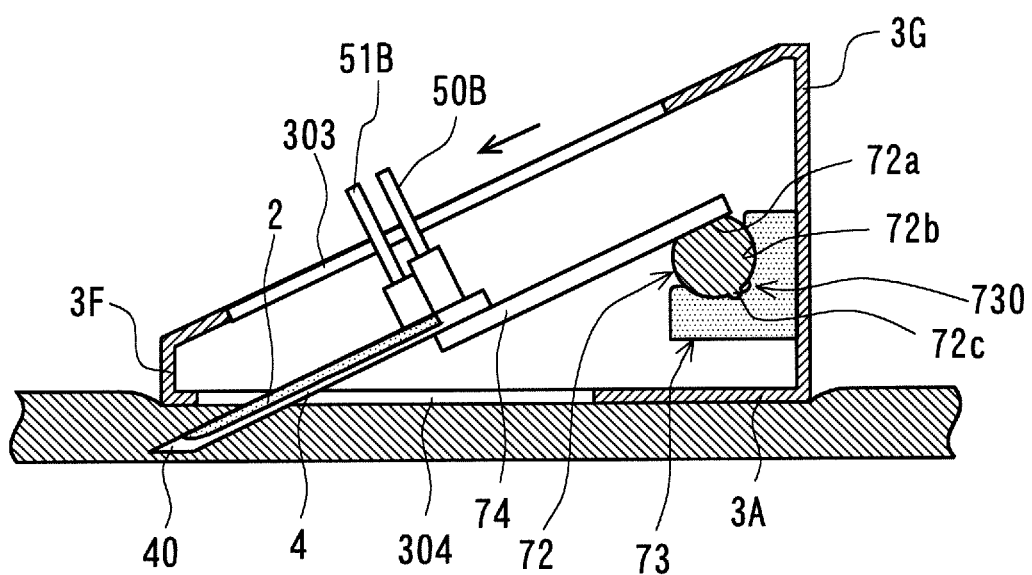
FIG. 25 is an explanatory diagram explaining the operation upon inserting the puncture sheet blade and the sensor under the skin.

FIG. 25 is an explanatory diagram explaining the operation upon inserting the puncture sheet blade 4 and the sensor 2 under the skin. As shown in FIG. 25, the user slides the blade knob 50B to the front end side of the slide opening 303 upon puncturing the skin with the puncture sheet blade 4 and implanting the sensor 2 under the skin. Consequently, the puncture sheet blade 4 in a state of integrally receiving the sensor 2 will slide on the guide rail 74, and the blade edge part 40 of the puncture sheet blade 4 is delivered from the lower surface opening 304 toward the skin. It is thereby possible to puncture the skin with the puncture sheet blade 4 and implant the sensor 2 under the skin.

The operation method of the puncture angle adjustment mechanism upon changing the puncture angle of the puncture sheet blade 4 is now explained with reference to FIG. 22, FIG. 26A, and FIG. 26B. Foremost, as shown in FIG. 22, the angle adjustment knob 71 is provided with a positioning mark 71a on the knob side. Moreover, of the side surface 3D of the housing 3, positioning marks 315a, 315b on the housing 3 side are provided around the operation opening 313. The user can change the puncture angle of the puncture sheet blade 4 and the insertion angle of the sensor by changing the positioning target to either the positioning mark 315a or 315b on the housing 3 side relative to the positioning mark 71a of the angle adjustment knob 71.

Figure 26A:
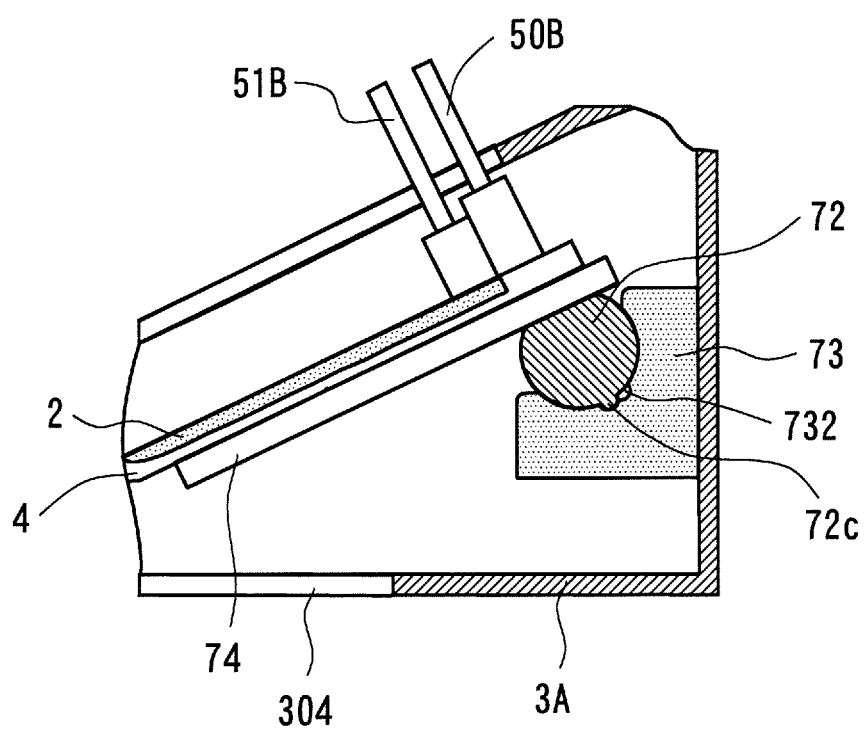
FIG. 26A is a first explanatory diagram explaining the operation method of the puncture angle adjustment mechanism.
Figure 26B:
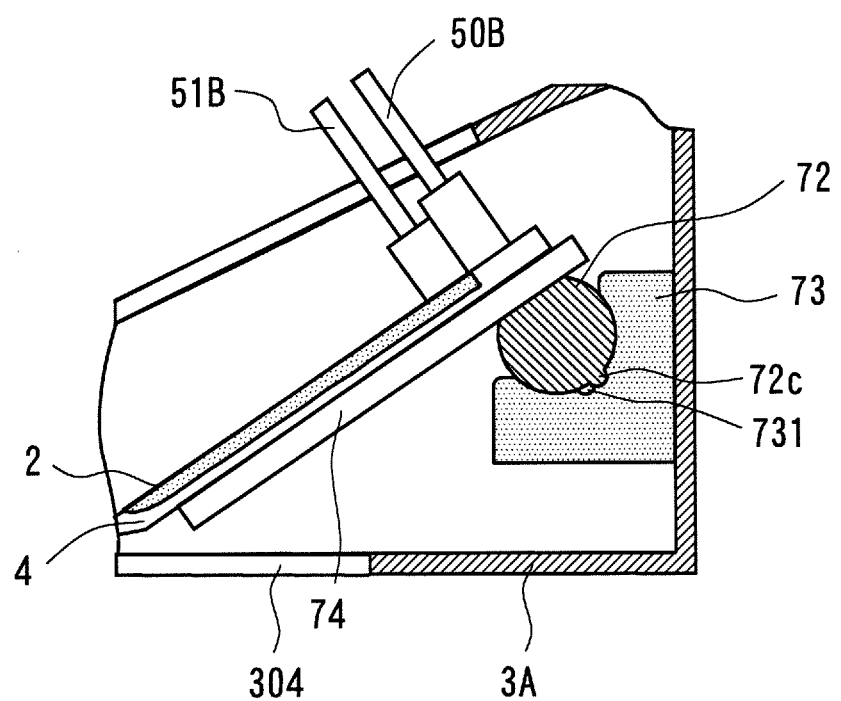
FIG. 26B is a second explanatory diagram explaining the operation method of the puncture angle adjustment mechanism.

In the state shown in FIG. 26A, the convex part 72c of the angle adjustment shaft part 72 is fitted in the first concave part 731 of the bearing member 73. Moreover, in the state shown in FIG. 26B, the convex part 72c of the angle adjustment shaft part 72 is fitted in the second concave part 732 of the bearing member 73. Since the guide member 74 which slidably supports the puncture sheet blade 4 is fixed to the planar surface part 72a of the angle adjustment shaft part 72, the inclination angle of the guide member 74 is changed as a result of whether the convex part 72c is fitted in the first concave part 731 or the second concave part 732. Specifically, when the convex part 72c of the angle adjustment shaft part 72 is fitted in the first concave part 731, the inclination angle formed by the under surface 3A of the housing 3 and the guide member 74 becomes smaller in comparison to the face of being fitted in the second concave part 732, and the puncture angle of the puncture sheet blade 4 and the inclination angle of the sensor will be reduced (become shallow).

As described above, the angle adjustment knob 71 is mounted coaxially at the end of the angle adjustment shaft part 72. Thus, of the first concave part 731 and the second concave part 732, the counterpart to which the convex part 72c of the angle adjustment shaft part 72 will be fitted can be switched by rotating the angle adjustment knob 71. When the positioning mark 71a of the angle adjustment knob 71 is positioned at the positioning mark 315a on the housing 3 side, the convex part 72c of the angle adjustment shaft part 72 will be fitted in the first concave part 731. Meanwhile, when the positioning mark 71a of the angle adjustment knob 71 is positioned at the positioning mark 315b on the housing 3 side, the convex part 72c of the angle adjustment shaft part 72 will be fitted in the second concave part 732.

According to the above, the user can rotate the angle adjustment knob 71 to position the positioning mark 71a to the positioning mark 315a on the housing 3 side when the user wishes to reduce the puncture angle (achieve a more shallow puncture angle) of the puncture sheet blade 4. Meanwhile, when the user wishes to increase (achieve a tighter puncture angle) of the puncture sheet blade 4, the user can rotate the angle adjustment knob 71 and position the positioning mark 71a to the positioning mark 315b on the housing 3 side. According to the above, the user can freely select and change the puncture angle of the puncture sheet blade 4; that is, the insertion angle of the sensor 2.

Note that, as shown in FIG. 24, with the puncture angle adjustment mechanism according to this embodiment, the movable range of the puncture angle of the puncture sheet blade 4 is restricted to be within the range where the concave part 730 of the bearing member 73 is formed. Accordingly, for example, if the movable range of the puncture angle is to be increased in comparison to the foregoing configuration example, for example, the number of concave parts 730 to be lined up may be increased. Moreover, since the puncture angle of the puncture sheet blade 4 can be changed based on the number of concave parts 730, it is possible to flexibly deal with the user's demands.

Other Embodiments

Moreover, with the sensor insertion and removing device according to each of the foregoing embodiments, although a case of housing a single sensor 2 inside the housing 3 is explained, a plurality of (for example, around five or so) sensors 2 can also be housed in the housing 3. In the foregoing case, preferably, a mechanism capable of inserting an unused sensor 2 under the skin while removing a certain used sensor 2 from under the skin into the housing 3 is provided. It is thereby possible to continue monitoring the target component without having to remove the sensor insertion and removing device from the skin surface over a long period.

The embodiments of the present invention were explained above, but the sensor insertion and removing device and the sensor insertion and removing method according to the present invention are not limited thereto, and may include the combinations thereof wherever possible. Moreover, the foregoing embodiments may be variously modified to the extent that they do not deviate from the gist of the present invention. For example, with the sensor insertion and removing device according to each of the foregoing embodiments, although a case was explained where the user performs manual operations, the sensor insertion and removing device may also be operated using another drive source such as electric power. Moreover, the explanation of the sensor insertion and removing device in each of the foregoing embodiments doubles as the explanation of the sensor insertion and removing method.

DESCRIPTION OF THE REFERENCE SIGNS

1, 1A, 1B, 1C . . . sensor insertion and removing device
2 . . . sensor
3 . . . housing
4 . . . puncture sheet blade
21 . . . sensor substrate
22 . . . sensor electrode
50 . . . sheet blade holder
50A . . . first joint part
50B . . . sheet blade knob
51 . . . sensor holder
51A . . . second joint part
51B . . . sensor knob
100 . . . monitoring device
200 . . . control unit
303 . . . slide opening
304 . . . lower surface opening
305 . . . guide groove

What is claimed is:

1. A sensor insertion and removing device, comprising:
a sensor;
a puncture blade member;
a housing which houses the sensor and the puncture blade member;
a guide part which is provided within the housing and which glidibly supports the puncture blade member;
a puncture blade operating part including a first grip part which is fixed to a predetermined first basic portion in the puncture blade member, and inserted through an operation opening so as to be exposed outside the housing;
a sensor operating part including a second grip part which is fixed to a predetermined second basic portion in the sensor, and inserted through the operation opening so as to be exposed outside the housing;
wherein the puncture blade operating part delivers the puncture blade member integrally with the sensor towards the outside of the housing in coordination with the movement of the first grip part to a first direction with respect to the housing, and removes the puncture blade member into the housing in coordination with the movement of the first grip part to a second direction which is opposite the first direction, and the sensor operating part delivers the sensor towards the outside of the housing in coordination with the movement of the second grip part driven by the movement of the first grip part to the first direction with respect to the housing, and removes the sensor into the housing in coordination with the movement of the second grip part to the second direction.

2. The sensor insertion and removing device according to claim 1, wherein the puncture blade member includes a concave part for slidably receiving the sensor along a longitudinal direction of the puncture blade member, and when the puncture blade operating part causes the puncture blade member to glide along the guide part integrally with the sensor, the sensor is maintained in a fitted state of being fitted in the concave part of the puncture blade member, and the fitted state is released when the puncture blade operating part causes the puncture blade member to glide along the guide part in a state of being separated from the sensor.

3. The sensor insertion and removing device according to claim 2, wherein the depth of the concave part is set to be equal to or greater than the thickness of the sensor.

4. The sensor insertion and removing device according to claim 3, wherein the sensor has a distal end having a distal end surface, said distal end surface of the sensor is inclined toward a base end side of the sensor from an exposed surface, which is on an opposite side to a contact surface which comes in contact with a bottom surface of the concave part, to the contact surface.

5. The sensor insertion and removing device according to claim 2, wherein the sensor has a distal end having a distal end surface, said distal end surface of the sensor is inclined toward a base end side of the sensor from an exposed surface, which is on an opposite side to a contact surface which comes in contact with a bottom surface of the concave part, to the contact surface.

6. The sensor insertion and removing device according to claim 1, wherein the guide part includes a linear guide part which is formed linearly, and the operation opening in the housing is formed linearly so as to oppose the linear guide part, the gliding operation of the puncture blade member is performed in conjunction with the sliding operation of the first grip part through the operation opening, and the removing operation of the sensor is performed in conjunction with the sliding operation of the second grip part through the operation opening.

7. The sensor insertion and removing device according to claim 1, wherein the guide part includes an arc-shaped guide part which is formed in an arc shape, the gliding operation of the puncture blade member is performed in conjunction with rotational operation of the first grip part, and the removing operation of the sensor is performed in conjunction with rotational operation of the second grip part.

8. The sensor insertion and removing device according to claim 1, wherein the puncture blade operating part has a first surface and the sensor operating part has a second surface, said first surface and said second surface mutually come in contact only during the operation, by the puncture blade operating part, of delivering the puncture blade member outside the housing.

9. The sensor insertion and removing device according to claim 1, further comprising:

a first restricting part which restricts the operation, by the puncture blade operating part, of delivering the puncture blade member outside the housing, wherein the first restricting part is provided so that the sensor reaches a predetermined target insertion depth at a point in time when restriction by the first restricting part is started.

10. The sensor insertion and removing device according to claim 9, wherein the sensor operating part further includes a locking pin which is biased toward an inner wall surface of the housing by an elastic member, and the inner wall surface of the housing is provided with a locking hole to which the locking pin is fitted at the point in time when restriction by the first restricting part is started.

11. The sensor insertion and removing device according to claim 1, wherein the guide part is axially supported in a swingable manner relative to the housing, the sensor insertion and removing device further comprising a puncture angle adjustment unit for adjusting a puncture angle of the puncture blade member by changing a swing stop position of the guide part relative to the housing.

12. A sensor insertion and removing method, comprising the steps of:

a setup step of setting, on skin, a sensor insertion and removing device, which comprises a sensor; a puncture blade member; a housing which houses the sensor and the puncture blade member; a guide part which is provided within the housing and which glidably supports the puncture blade member; a puncture blade operating part including a first grip part which is fixed to a predetermined first basic portion in the puncture blade member, and inserted through an operation opening so as to be exposed outside the housing; and a sensor operating part including a second grip part which is fixed to a predetermined second basic portion in the sensor, and inserted through the operation opening so as to be exposed outside the housing;

a sensor insertion step of inserting, after the setup step, the sensor under the skin by causing the puncture blade member to glide along the guide part integrally with the sensor, upon delivering the puncture blade member outside the housing to puncture the skin in coordination with the movement of the first grip part to a first direction with respect to the housing;

a puncture blade removing step of removing, after the sensor insertion step, the puncture blade member from under the skin into the housing by causing the puncture blade member to glide along the guide part in a state of being separated from the sensor in coordination with the movement of the first grip part to a second direction which is opposite to the first direction; and a sensor removing step of removing, after the puncture blade removing step, the sensor from under the skin into the housing by pulling the sensor out from under the skin in coordination with the movement of the second grip part to the second direction.

13. The sensor insertion and removing method according to claim 12, wherein the puncture blade member includes a concave part for slidably receiving the sensor along a longitudinal direction of the puncture blade member, in the sensor insertion step, the sensor is maintained in a fitted state of being fitted in the concave part of the puncture blade member, and in the puncture blade removing step, the fitted state is released.

14. The sensor insertion and removing method according to claim 12, the guide part is axially supported in a swingable manner relative to the housing, the sensor insertion and removing method further comprising a puncture angle adjustment step of adjusting a puncture angle of the puncture blade member by changing a swing stop position of the guide part relative to the housing before the sensor insertion step.

* * * * *